US009889168B2

(12) United States Patent
Luytjes et al.

(10) Patent No.: US 9,889,168 B2
(45) Date of Patent: Feb. 13, 2018

(54) RESPIRATORY SYNCYTIAL VIRUS WITH A GENOMIC DEFICIENCY COMPLEMENTED IN TRANS

(71) Applicant: De Staat der Nederlanden, vert, door de minister van VWS, The Hague (NL)

(72) Inventors: Willem Luytjes, Soest (NL); Myra Noorely Widjojoatmodjo, Zeist (NL)

(73) Assignee: De Staat der Nederlanden, vert, door de minister van VWS, The Hague (NL)

( * ) Notice: Subject to any disclaimer, the term of this patent is extended or adjusted under 35 U.S.C. 154(b) by 0 days.

(21) Appl. No.: 14/815,131

(22) Filed: Jul. 31, 2015

(65) Prior Publication Data

US 2015/0329833 A1 Nov. 19, 2015

Related U.S. Application Data

(62) Division of application No. 10/583,800, filed as application No. PCT/NL2004/000911 on Dec. 24, 2004, now Pat. No. 9,107,939.

(30) Foreign Application Priority Data

Dec. 24, 2003 (WO) ................ PCT/NL2003/000930

(51) Int. Cl.

| | |
|---|---|
| ***A61K 39/155*** | (2006.01) |
| ***A61K 35/76*** | (2015.01) |
| ***C07K 14/005*** | (2006.01) |
| ***C12N 7/00*** | (2006.01) |
| ***A61K 39/12*** | (2006.01) |
| *A61K 39/00* | (2006.01) |

(52) U.S. Cl.

CPC .............. *A61K 35/76* (2013.01); *A61K 39/12* (2013.01); *A61K 39/155* (2013.01); *C07K 14/005* (2013.01); *C12N 7/00* (2013.01); *A61K 2039/5252* (2013.01); *A61K 2039/543* (2013.01); *C12N 2760/18521* (2013.01); *C12N 2760/18522* (2013.01); *C12N 2760/18532* (2013.01); *C12N 2760/18534* (2013.01); *C12N 2760/18552* (2013.01); *C12N 2760/18561* (2013.01); *C12N 2760/18562* (2013.01)

(58) Field of Classification Search

None

See application file for complete search history.

(56) References Cited

U.S. PATENT DOCUMENTS

| | | | |
|---|---|---|---|
| 6,033,886 | A | 3/2000 | Conzelmann |
| 6,264,957 | B1 | 7/2001 | Collins |
| 2005/0186224 | A1 | 8/2005 | Buchholz et al. |

FOREIGN PATENT DOCUMENTS

| | | | |
|---|---|---|---|
| WO | WO-96/10400 | A1 | 4/1996 |
| WO | WO-98/02530 | A1 | 1/1998 |
| WO | WO-00/053766 | A1 | 3/2000 |
| WO | WO-03/029416 | A2 | 4/2003 |

OTHER PUBLICATIONS

Teng et al., Journal of Virology. 1998 vol. 72, pp. 5707-5716.*

Teng et al. Virology 2001, vol. 289, pp. 283-296.*

Collins et al. "Evaluation in chimpanzees of vaccinia virus recombinants that express the surface glycoproteins of human respiratory syncytial virus" Vaccine, vol. 8, Apr. 1990, pp. 164-168.

Collins et al. "Production of infectious human respiratory syncytial virus from cloned cDNA confirms an essential role for the transcription elongation factor from the 5' proximal open reading frame of the M2 mRNA in gene expression and provides a capability for vaccine development", Proceedings of the National Academy of Sciences, vol. 92, Dec. 1995, pp. 11563-11567.

Connors, et al. "Respiratory Syncytial Virus (RSV) F, G, M2 (22K), and N Proteins Each Induce Resistance to RSV Challenge, but Resistance Induced by M2 and N Proteins is Relatively Short-Lived", Journal of Virology (Mar. 1991), vol. 65, No. 3, pp. 1634-1637.

Elliott et al. "Characterization of Recombinant Respiratory Syncytial Viruses with the Region Responsible for Type 2 T-Cell Responses and Pulmonary Eosinophilia Deleted from the Attachment (G) Protein", Journal of Virology, vol. 78, No. 16, Aug. 2004, pp. 8446-8454.

Karron et al., "Respiratory syncytial virus (RSV) SH and G proteins are not essential for viral replication in vitro: Clinical evaluation and molecular characterization of a cold-passaged, attenuated RSV subgroup B mutant", PNAS, 1997, vol. 94 (25), pp. 13961-13966.

Kimpen, "Prevention and treatment of respiratory syncytial virus bronchiolitis and postbronchiolitic wheezing", Respiratory Research (2002), vol. 3, Suppl 1, pp. S40-S45.

Neumann et al. "A decade after the generation of a negative-sense RNA virus from cloned cDNA—what have we learned?", Journal of General Virology, vol. 82, 2002, pp. 2635-2662.

Openshaw et al. "Links between respiratory syncytial virus bronchiolitis and childhood asthma: clinical and research approaches", The Pediatric Infectious Disease Journal, vol. 22, No. 2, 2003, pp. S58-65.

(Continued)

*Primary Examiner* — Shanon A Foley
*Assistant Examiner* — Myron Hill
(74) *Attorney, Agent, or Firm* — Gilberto M. Villacorta; Sunit Talapatra; Foley & Lardner LLP

(57) ABSTRACT

The invention relates to pneumoviral virions comprising a viral genome that has a mutation in a gene coding for a protein that is essential for infectivity of the pneumovirus, whereby the mutation causes a virus produced from only the viral genome to lack infectivity, and whereby the virion comprises the protein in a form and in an amount that is required for infectivity of the virion. The invention also relates to methods for producing the pneumoviral virions and for using the virions in the treatment or prevention of pneumoviral infection and disease. A preferred pneumoviral virion is a virion of Respiratory Syncytial Virus in which preferably the gene for the G attachment protein is inactivated and complemented in trans.

3 Claims, 5 Drawing Sheets

(56) References Cited

OTHER PUBLICATIONS

Plotnicky et al. "Enhanced pulmonary immunopathology following neonatal priming with formalin-inactivated respiratory syncytial virus but not with the BBG2NA vaccine candidate" Vaccine, vol. 21, 2003, pp. 2651-2660.

Power et al. "Induction of Protective Immunity in Rodents by Vaccination with a Prokaryotically Expressed Recombinant Fusion Protein Containing a Respiratory Syncytial Virus G Protein Fragment", Virology, vol. 230, 1997, pp. 155-166.

Prince, et al. "Vaccine-enhanced respiratory syncytial virus disease in cotton rats following immunization with Lot 100 or a newly prepared reference vaccine", Journal of General Virology (2001), vol. 82, pp. 2881-2888.

Schmidt et al. "Mucosal Immunization with Live Recombinant Bovine Respiratory Syncytial Virus (BRSV) and Recombinant BRSV Lacking the Envelope Glycoprotein G Protects against Challenge with Wild-Type BRSV", Journal of Virology, vol. 76, No. 23, Dec. 2002, pp. 12355-12359.

Srikiatkhachorn et al. "Virus-specific CD8 T Lymphocytes Down regulate T Helper Cell Type 2 Cytokine Secretion and Pulmonary Eosinophilia during Experimental Murine Respiratory Syncytial Virus Infection" The Journal of Experimental Medicine, vol. 186, No. 3, Aug. 4, 1997, pp. 421-432.

Srikiatkhachorn et al. "Virus-Specific Memory and Effector T Lymphocytes Exhibit Different Cytokine Responses to Antigens during Experimental Murine Respiratory Syncytial Virus Infection", Journal of Virology, vol. 71, No. 1, Jan. 1997, pp. 678-685.

Stokes Peebles et al. "The Complex Relationship between Respiratory Syncytial Virus and Allergy in Lung Disease." Viral Immunology, vol. 16, No. 1, 2003, pp. 25-34.

Techaarpornkul et al. "Functional Analysis of Recombinant Respiratory Syncytial Virus Deletion Mutants Lacking the Small Hydrophobic and/or Attachment Glycoprotein Gene" Journal of Virology, vol. 75, No. 15, Aug. 2001, pp. 6825-6834.

Teng et al. "Contribution of the Respiratory Syncytial Virus G Glycoprotein and Its Secreted and Membrane-Bound Forms to Virus Replication in Vitro and in Vivo" Virology, vol. 289, 2001, pp. 283-296.

Teng et al. "Identification of the Respiratory Syncytial Virus Proteins Required for Formation and Passage of Helper-Dependent Infectious Particles", Journal of Virology, vol. 72, No. 7, Jul. 1998, pp. 5707-5716.

* cited by examiner

RESPIRATORY SYNCYTIAL VIRUS WITH A GENOMIC DEFICIENCY COMPLEMENTED IN TRANS

CROSS REFERENCE TO RELATED APPLICATIONS

The present application is a Divisional of U.S. application Ser. No. 10/583,800, which is a U.S. National Stage of International Application No. PCT/NL2004/000911, filed Dec. 24, 2004, and which claims benefit to International Application No. PCT/NL2003/00930 filed Dec. 24, 2003, the entire disclosures of which are incorporated herein by reference.

The instant application contains a Sequence Listing which has been submitted in ASCII format via EFS-WEB and is hereby incorporated by reference in its entirety. Said ASCII copy, created on Apr. 11, 2017 is named SequenceListing.txt and is 32 KB.

FIELD OF THE INVENTION

The present invention relates to the field of vaccination, and more specifically to vaccines against disease caused by pneumoviruses such as e.g. Respiratory Syncytial Virus (RSV). The invention pertains RSV virions carrying an RSV genome in which a gene that is essential for infectivity has been inactivated, while the corresponding wild type gene-product is complemented in trans to the virion. The invention further relates to methods for the production of such RSV virions and to their use in vaccines and methods for vaccination against pneumoviruses.

BACKGROUND OF THE INVENTION

Human respiratory Syncytial virus is classified in the genus Pneumovirus, family Paramyxoviruses. It is a major cause of severe lower respiratory tract disease in infants, the elderly and in immunocompromised individuals. It is also an important factor in upper respiratory tract disease in older children and adults. Currently there is no effective h-RSV vaccine available in the art.

RSV is an enveloped RNA virus that expresses two major antigens at its surface: the attachment protein G and the fusion protein F. Both proteins appear to invoke protective antibodies. G is the determinant of the two known h-RSV subgroups A and B. Antigenic differences can be found within the two groups. The G protein shows a high degree of variation with only 53% amino acid homology between groups A and B and up to 20% differences in G protein sequences within group A (Mufson 1988, Cane 1991).

Passive immunisation with RSV-enriched immunoglobulin (Respigam) or synthetic humanised monoclonal antibodies against F (Palivizumab) is currently used to treat and protect neonates of certain predispositions (e.g. premature birth) against RSV infection (Robinson 2000, Greenough 2000). RSV pathology has two major aspects: cell damage caused by the virus itself and tissue damage caused by the overreacting immune system. The latter is a highly complicating factor in vaccine design.

RSV infections are seasonal, limited to the winter period and peak in the Northern Hemisphere around the end of the year. RSV infects every child before the age of two, in many cases twice. Older individuals on average are infected every other year, depending on the setting; people in close contact with infants and young children have a 50% risk. The virus spreads by close contact, in droplets or through contaminated surfaces. RSV is not efficiently spread through aerosols; the virus particles are relatively unstable. Internal spread of the virus from the upper respiratory tract (URT) to the lower respiratory tract (LRT) occurs predominantly by inhalation of virus particles produced in the URT epithelium during primary infection. Spread through syncytium formation (one of the pathological properties of the virus, which gave it its name) can not be ruled out and may play a secondary role in LRT infection.

In general, RSV pathology starts in the URT; the port of entry is the nose and to a lesser extent the eyes—not the mouth. When restricted to URT tissues, disease is limited to common cold, although in adults sometimes severe. However, when the virus can reach the LRT, bronchiolitis and pneumonia can ensue in unprotected individuals. In young infants, this can be life threatening, approx. 1/100 will require hospitalisation and mechanical ventilation, out of these 1% may die. In the elderly, RSV-induced LRT disease is a major cause of hospitalisation; it is suspected that RSV causes 25% of flu-like diseases.

The immune response to RSV is complex. In general, exposure to h-RSV will build up a response that protects against LRT disease. This response wanes with older age, causing the higher susceptibility to RSV of the older population. Effective long lasting protection against URT disease appears not feasible: re-infection is very common, even within the same season and this is not caused by viral variation. Protection against RSV infection involves antibodies against viral proteins F and G circulating in the blood, which can prevent LRT disease. URT infection can be controlled by mucosal antibodies against F and G, but these have a limited life span. CD8+ T cells against as yet unidentified viral proteins are required to clear the virus from infected tissues, but they appear to be short-lived or inefficiently recruited from their reservoirs. Most likely, this is caused by RSV-expressed factors, possibly encoded in the G gene (Srikiatkhachorn, 1997a).

An important aspect of RSV disease is immune enhancement of pathology. In limited cases the cellular immune response can exacerbate RSV disease by the action of cytokines on infected tissues released from excessively attracted granulocytes. Host predisposition is involved in this reaction, but possibly also the timing of first RSV infection after birth. Unfortunately, early vaccine trials with formalin-inactivated RSV showed that in these vaccination settings immune enhanced pathology upon wt infection was prevalent (Kim 1969). Factors contained in RSV appear to be responsible for this phenomenon and were apparently released by formalin treatment. In the 40 years since then, it was gradually shown that the viral G protein is the predominant mediator of these problems, but the mechanism remains unclear (Srikiatkhachorn 1997b). In any case, vaccination with a G protein out of the context of the virion (i.e. in inactivated virus preparations, as expression product not properly embedded in a membrane or in the form of peptides) seems to be causing immune enhancement in model systems. Thus, although G contributes to some extent to RSV immunity, its properties also complicate vaccine design.

Initial live RSV vaccine candidates included cold passaged or temperature-sensitive mutants. The former have been attenuated by culturing at decreasing temperature, leading to dependency on low temperatures for growth, whereas the latter mutants have been made dependent on a specific, usually higher temperature for replication by chemical or radiation mutagenesis. These live virus vaccine candidates appeared to be either under- or overattenuated (Crowe 1998).

Subunit vaccine candidates are derived from either the RSV-F or the G protein, being the main targets for neutralising antibodies. A candidate subunit vaccine, PFP2, purified F protein, is safe in RSV-seropositive patients, but it did not provide full protection against LRT infection and associated disease (Gonzalez 2000). Another subunit vaccine approach is BBG2Na, which consists of a polypeptide, comprising amino acid 130-230 of h-RSV-G, fused to the albumin-binding domain of streptococcal G protein (Power 1997). BBG2Na induces a T helper type 2 response in neonatal mice, and does not elicit lung immunopathology (Siegrist 1999). There is no data yet on protection. The use of new adjuvants for a balanced humoral and cellular immune response are currently under investigation in animal models (Plotnicky 2003).

The use of plasmid-DNA vectors encoding RSV-F and G antigens as vaccine candidates has been studied in animal models. These vaccines induce protective responses in rodents (Li 2000), but in one study RSV-F DNA vaccine candidate immunised mice developed a slightly enhanced pulmonary inflammatory response following challenge with wt virus (Bembridge 2000). The feasibility of the use of plasmid DNA vaccines in humans is not yet known and it will likely take at least 15 years before this approach is sufficiently studied and—more importantly—accepted, particularly for neonates. Candidate vaccines based on vector delivery systems are constructed of live recombinant vectors expressing RSV proteins. For example, recombinant vaccinia virus expressing RSV-F and G provided protection in mice, but lacked this effect in chimpanzees (Collins 1990). The question is whether these systems are safe (notably vaccinia virus) and feasible in the light of existing (maternal) antibodies against poxviruses in the community and the main target group being neonates.

Several vaccine candidates are based on recombinant live RSV, generated by reverse genetics. One line of study focuses on attenuating these viruses by introducing the individual or combined mutations responsible for cold-adaptation and temperature-sensitivity into the recombinant virus. None of these vaccine candidates were usable, because of either over- or underattenuation. Another line of study focuses on deletion of one or more viral non-structural genes. Limited data are available on the behaviour of these viruses in model systems (Jin 2003).

An alternative approach to RSV vaccine development is the use of bovine RSV. A chimeric bovine RSV with either the human F protein alone or both the human F and G protein was evaluated for its efficacy in chimpanzees. This vaccine candidate was restricted in replication to such a degree that animals were not protected after wild type h-RSV challenge (Buchholtz 2000).

Thus, currently there is no effective h-RSV vaccine available in the art. All RSV vaccine candidates that have been tested in animal models are unusable in humans. There is thus a long felt need in the art for RSV vaccines that are both effective and safe and it is an object of the present invention to provide for such vaccines.

DESCRIPTION OF THE INVENTION

Definitions

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The term "virion" as used herein refers to a virus particle that contains the nucleocapsid protein, the viral genome and the replicase complex in a lipid envelop that contains the viral structural glycoproteins.

The terms "infectivity of a virus", "infectious virus", "infectious virus particle" or "infectious virion" denote viruses, virus particles or virions that are capable of entering suitable host cells and initiating a virus replication cycle, whether or not this leads to the production new virus that is infectious.

DETAILED DESCRIPTION OF THE INVENTION

In a first aspect the present invention relates to a virion of a pneumovirus. The virion comprises a viral genome that has a mutation in a gene coding for a protein that is essential for infectivity of the pneumovirus, whereby the mutation causes a virus produced from only the viral genome to lack infectivity, and whereby the virion comprises the protein in a form and in an amount that is required for infectivity of the virion.

The pneumovirus preferably is a Respiratory Syncytial Virus (RSV), more preferably a human or bovine RSV. The human RSV may either be a subgroup A or B virus, and preferably is a clinical isolate, more preferably an isolate that has not been extensively passaged in vitro (preferably passaged less than 10, 8, 6 or 5 times as descrined in the Examples). Therefore, any RSV strain or isolate may be used in the context of the present invention, whereby is understood that the invention is only exemplified by means of the particular human RSV isolate 98-25147-X, referred to as RSV isolate X. Further preferred is that virus is a recent clinical isolate whereby recent is defined as being first isolated less than 10, 8, 6, 4, 3, or 2 years ago. It will be understood that although the nucleotide sequences in the virion do not need to correspond to those of the recent isolate, preferably, the amino acid sequences of the proteins present in the virion of the invention are identical to the proteins as they occur in a recent clinical isolate.

The viral genome comprises at least one mutation in at least one viral gene coding for a protein that is essential for infectivity of the pneumovirus, whereby the infectivity of the virus is as defined above. Thus, the protein that is essential for infectivity of the pneumovirus is a protein that is essential for the capability of the virion of the invention to enter a suitable host cell and initiate a viral replication cycle, whereby the replication cycle does not necessarily lead to the production of new infectious virions. In preferred virions of the invention the mutation causes the virion to lack infectivity in vivo, i.e. in a suitable host organism, whereby the virions may still be infectious for suitable host cells cultured in vitro.

In a preferred virion of the invention, the mutated gene that codes for a protein essential for infectivity of the pneumovirus, is a gene, which codes for a structural protein of the virus. A structural protein of a pneumovirus is herein understood to be a protein that is present in virions of wild-type infectious virus. Preferred genes coding for structural proteins to be mutated in the virions of the invention are the genes coding for the attachment protein G and/or the fusion protein F, whereby the G protein is most preferred. Deletion and/or functional inactivation the gene coding for G protein serves several purposes and prevents a number of problems and complications of current RSV vaccine candidates. One purpose is vaccine safety: RSV without G protein is highly attenuated in its host (Karron 1997, Schmidt 2002) because it will not be able to efficiently infect host cells. One complication is that the G protein is strongly implicated in causing undesired immunological responses, including enhanced immune pathology (Alwan 1993, Srikiatkhachorn 1997b) and possible skewing of the immune system towards an allergy (and asthma-) prone state under certain genetic predispositions (Openshaw 2003, Peebles 2003). This will be prevented by deletion or inactivation of the G gene. A pneumoviral virion of the invention comprising a viral genome that has an inactivating mutation in the gene coding for a G attachment protein, and comprising the G attachment protein in a form and in an amount that is required for infectivity of the virion is referred to as a "ΔG+G" (pneumo) virus or virion. Similarly, the virion that has the inactivating mutation in the gene coding for a G attachment protein, but which is not complemented in trans with a functional amount of G protein is referred to as a "ΔG" (pneumo)virus or virion.

The pneumoviral virions of the invention are thus transiently and functionally reconstituted with an externally encoded protein that is essential for infection. Preferably the externally encoded protein that is essential for infection is the attachment protein G and/or the fusion protein F, whereby the G protein is most preferred. Preferably the externally encoded protein that is essential for infection is of the same viral subgroup (A or B) as the genome that is present in the virion. More preferably the externally encoded protein that is essential for infection is homologous to the genome that is present in the virion, whereby is meant that the protein has the same amino acid sequence as the amino acid sequence that was encoded in the genome of the virus prior to its inactivation. Alternatively, this may mean that the externally encoded protein has the same amino acid sequence as present in a wild type virion of which the amino acid sequences with one or more internally encodes proteins have 100% identity with their counter part in the virion of the invention.

In the virions of the invention, the mutation in the gene of the essential structural protein is a mutation that causes the virus produced from only the viral genome to lack the protein or to express a biologically inactivated protein. Production of virus from only the viral genome is understood to mean virus produced exclusively from the viral genome as present in the virions and in the absence of any coding sequence complementing the viral genome in trans. The viral genome as present in the virions is thus incapable of directing expression of the essential structural protein. This may be achieved in various ways known to the skilled person, including e.g. inactivation of the translation initiation codon, introduction of stop codons near the N-terminus of the encoded protein, one or more frame-shift mutations, deletion of one or more fragments from the gene. Preferably the gene is inactivated by deletion of at least 10, 20, 50, 75, 90 or 95% of the sequence coding for the essential structural protein. Most preferred is however, a virion in which the mutation comprises deletion of the (entire) sequence coding for the protein.

Explicitly included in the invention are virions in which more than one mutation is present. In particular, more than one viral protein-coding gene may comprise mutations that inactivate or alter the function of the protein in question, or which cause the protein to lack from the virions as described above. E.g. the cold-passaged or heat-sensitive mutations as known in the art may be combined with inactivation of the essential structural proteins as disclosed in the invention above.

Clearing of pneumoviruses like RSV from the infected host organisms requires proper cellular immunity, which will not be effectively mounted without infection of epithelial cells by the virus. However, the mutant pneumoviruses of the invention lack genetic information for a protein that is essential for infection of host cells in vivo. Therefore the present invention discloses methods for the production of the mutant pneumoviruses, which include replication of mutant pneumoviruses in cells that complement (in trans) for the absence of the protein that is essential for infection.

In another aspect the invention thus pertains to a method for producing the above defined mutant pneumoviral virions. The method is a method for producing pneumoviral virions, whereby the virions comprise a viral genome that has a mutation in a gene coding for a protein that is essential for (in vivo) infectivity of the pneumovirus, whereby the mutation causes a virus produced from only the viral genome to lack infectivity, and whereby the virion comprises the protein in a form and in an amount that is required for infectivity of the virion. The method comprises the steps of: (a) infecting a culture of a first host cell with a pneumovirus comprising a viral genome that has a mutation as defined above, whereby the host cell comprises an expression vector which directs expression, either transiently or constitutively, in the host cell of the protein in a form and in an amount that is required for infectivity of the virion; and, (b) recovery of the virions from the infected host cell culture. Recovery of virions from the infected host cell culture may include either or both recovery from the culture medium as well as recovery from the cells.

The first host cell may be any host cell in which the pneumovirus is capable of replication, with or without the simultaneous expression in trans of the protein that is required for infectivity of the virion. Suitable host cells for this purpose are e.g. African green monkey kidney cell cultures (such as e.g. Vero, ECACC lot 10-87, $134^{th}$ passage, 1990, EMEA approved).

In a preferred method of the invention, the pneumovirus that is used to infect the culture of a first host cell culture, is produced in a method comprising the steps of: (a) providing to a second host cell one or more expression vectors which direct expression in the host cell of: (i) a viral genomic RNA that has a mutation in a gene coding for a protein that is essential for (in vivo) infectivity of the pneumovirus, whereby the mutation causes a virus produced from only the viral genome to lack infectivity; and, (ii) a pneumoviral polymerase enzyme complex and optionally one or more further viral proteins; and, (b) culturing the second host cell whereby the virions are produced. In a preferred method, the virions produced by the second host cell are amplified by one or more further cellular infection steps employing host cells which are the same or different from the second host cell.

The second host cell may be any host cell in which the pneumovirus is capable of replication, with or without the simultaneous expression in trans of the protein that is required for infectivity of the virion. Suitable host cells for this purpose are e.g. African green monkey kidney cell cultures (such as e.g. Vero, ECACC lot 10-87, $134^{th}$ passage, 1990, EMEA approved), or Hep-2 cells. The second host cell may be the same as or different from the first host cell.

In the methods of the invention, the viral genomic RNA is transcribed from a viral DNA copy that is under the control of a bacteriophage DNA-dependent RNA polymerase promoter and whereby the (second) host cell is provided with an expression vector which directs expression in the host cell of the bacteriophage DNA-dependent RNA polymerase. Preferably, the bacteriophage DNA-dependent RNA polymerase is a T7, T3 or SP6 polymerase.

The pneumoviral polymerase enzyme complex that is expressed from one or more expression vector(s) in the second host cell at least includes the L, P, N proteins expressed from their corresponding genes or cDNA's in the expression vector(s). For improved efficiency of viral assembly and packaging of the naked viral genomic RNA, optionally, one or more further viral proteins are expressed in the second host cells. Preferred viral proteins for this purpose include the viral matrix membrane proteins of which the M2-1 protein is particularly preferred. The L, P, N, M2-1, G or F proteins are preferably derived from the viral genome of the viral isolate which is introduced and expressed in the host cell, but alternatively also homologous proteins from other heterologous viral or non viral sources may be used.

The skilled person will appreciate that a wide variety of expression vectors and regulatory sequences (such as promoters) are available in the art for expression of the viral genomic RNA, the DNA-dependent RNA polymerase, pneumoviral polymerase enzyme complex and optional further viral proteins, as well as the essential structural protein, in the first and/or second host cells (see e.g. Sambrook and Russell (2001) "Molecular Cloning: A Laboratory Manual ($3^{rd}$ edition), Cold Spring Harbor Laboratory, Cold Spring Harbor Laboratory Press, New York).

For reverse genetics of RNA viruses, i.e. expression of a recombinant RNA virus such as the virions of the present invention, a cDNA copy of the viral genomic RNA is cloned into plasmids and is placed under the control of sequences that will allow synthesis of RNA from the DNA under certain conditions. Generally, the promoter sequence for bacteriophage RNA polymerase (e.g. the T7 RNA polymerase) is placed upstream of the DNA copy of the RNA genome, while an appropriate terminator for the RNA polymerase is placed downstream of the genome. Self-cleaving ribozyme sequences are placed upstream of the terminator sequences, to allow synthesis of RNA with the correct terminal nucleotides. Correct terminal sequences are generally required to rescue virus from the synthetic RNA. For non-segmented negative strand RNA viruses, co-expression of the polymerase enzyme complex (N, P and L proteins for Paramyxoviruses) along with the genomic or anti-genomic RNA is required to obtain recombinant virus (reviewed by Neumann 2002 and exemplified in the Examples herein).

Other preferred methods may comprise the further step of isolating and/or purifying the virions of the invention and/or formulating these virions into pharmaceutical compositions. Methods for isolating and/or purifying virions are well known to the skilled virologist. Such methods e.g. include various centrifugation techniques (e.g. differential or density centrifugation), or chromatographic techniques. A method for formulating the virions of the invention into a pharmaceutical composition at least comprises the step of mixing the virions with a pharmaceutically acceptable carrier as defined below.

In a further aspect the invention relates to a composition comprising a virion as defined above or obtainable in a method as defined above, and a pharmaceutically acceptable carrier. The composition preferably is a pharmaceutical composition that is preferably suitable for use as a vaccine, i.e. the composition preferably is a vaccine.

In a yet another aspect the invention provides for a pharmaceutical preparation comprising as active ingredient a virion according to the invention, and a pharmaceutically acceptable carrier. Pharmaceutically acceptable stabilising agents, osmotic agents, buffering agents, dispersing agents, and the like may also be incorporated into the pharmaceutical compositions. The preferred form depends on the intended mode of administration and therapeutic application. The pharmaceutical carrier can be any compatible, non-toxic substance suitable to deliver the reconstituted viral membranes to the patient. Pharmaceutically acceptable carriers for intranasal delivery are exemplified by water, buffered saline solutions, glycerin, polysorbate 20, cremophor EL, and an aqueous mixture of caprylic/capric glyceride, and may be buffered to provide a neutral pH environment.

For administration by inhalation, the pharmaceutical compositions of the present invention are conveniently delivered in the form of an aerosol spray from pressurised packs or a nebuliser, wherein the virions are present in a carrier as described for intranasal delivery but with the use of a suitable propellant, e.g., dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount.

Methods for preparing intranasal or inhalant compositions are well known in the art and described in more detail in various sources, including, for example, Remington's Pharmaceutical Science (15th ed., Mack Publishing, Easton, Pa., 1980) (incorporated by reference in its entirety for all purposes). The virions may thus be formulated as the active component in any preparation for vaccination, which may further e.g. include carriers, adjuvants, stabilisers, solubilisers, preservatives and other excipients known in the art, to allow or to aid efficient administration of the preparation for vaccination to individuals, preferably human and live stock or farm animals (such as cows, pigs, horses, goats, sheep).

In a further aspect, the invention relates to a method for vaccination against, or for prophylaxis or therapy (prevention or treatment) of an pneumoviral infection by administration of a therapeutically or prophylactically effective amount of (a pharmaceutical composition comprising) the virions of the invention as defined above, or obtainable as defined above, to a subject in need of prophylaxis or therapy. Preferably, the virions are administered intranasally.

The invention similarly relates to virions of the invention as defined above, or obtainable as defined above, for use as a medicament, preferably a medicament for vaccination against, or for prophylaxis or therapy of a pneumoviral infection. The invention further relates to the use of the virions of the invention in the manufacture of a medicament for vaccination against, or for prophylaxis or therapy of a pneumoviral disease or infection. Preferably the medicament is a preparation for intranasal administration.

The compositions comprising the virions of the invention for vaccination are preferably administered intranasally to appropriate hosts. In one embodiment, calves are to be protected from b-RSV infections. In yet another embodiment, humans, of which preferably infants and elderly or immune compromised individuals are protected from h-RSV infections. Formulations preferably comprise formulations suitable for administration as intranasal drops or spray, preferably a nasal spray. The ΔG+G-pneumoviral particles in the composition will infect epithelial cells of the upper respiratory tract only once because the second generation virions produced from the initially infected URT epithelial cells lack the G attachment protein for which the coding sequence has been removed from the genome. These ΔG-virions are therefore non-infectious in vivo in host organisms. However, the initial single cycle of infection allows for the development of appropriate cellular immunity—that is a response capable of clearing wild-type virus infection—to be mounted against pneumovirus, or RSV in particular, while protective antibodies against F—i.e. antibodies that will prevent lower respiratory tract infection—will be elicited by the vaccine and the non-infectious progeny. Anti-F antibodies are effective in limiting RSV infection, as is shown by the effectiveness of Palivimuzab treatment, which is a humanised monoclonal antibody against F. This is the basis of the efficacy of the recombinant live attenuated pneumoviral vaccines of the invention. These live viral vaccines solves a number of problems associated with current pneumovirus vaccine candidates. The presence of the G-protein in its natural context in the virion allows for the development of appropriate cellular immunity whereas the undesirable effects of immunity against the isolated G protein that is largely responsible for immune enhancement of b-RSV and h-RSV pathology in cattle and humans respectively, is avoided.

Intergenic region between L and M2-2: 6722-6792 of SEQ ID NO:1

Intergenic region between P and N: 12855-12899 of SEQ ID NO:1

Intergenic region between N and NS2: 14081-14127 of SEQ ID NO:1

Region of G gene deletion: 9607-9636 and 10532-10605 of SEQ ID NO:1.

Figure 3:
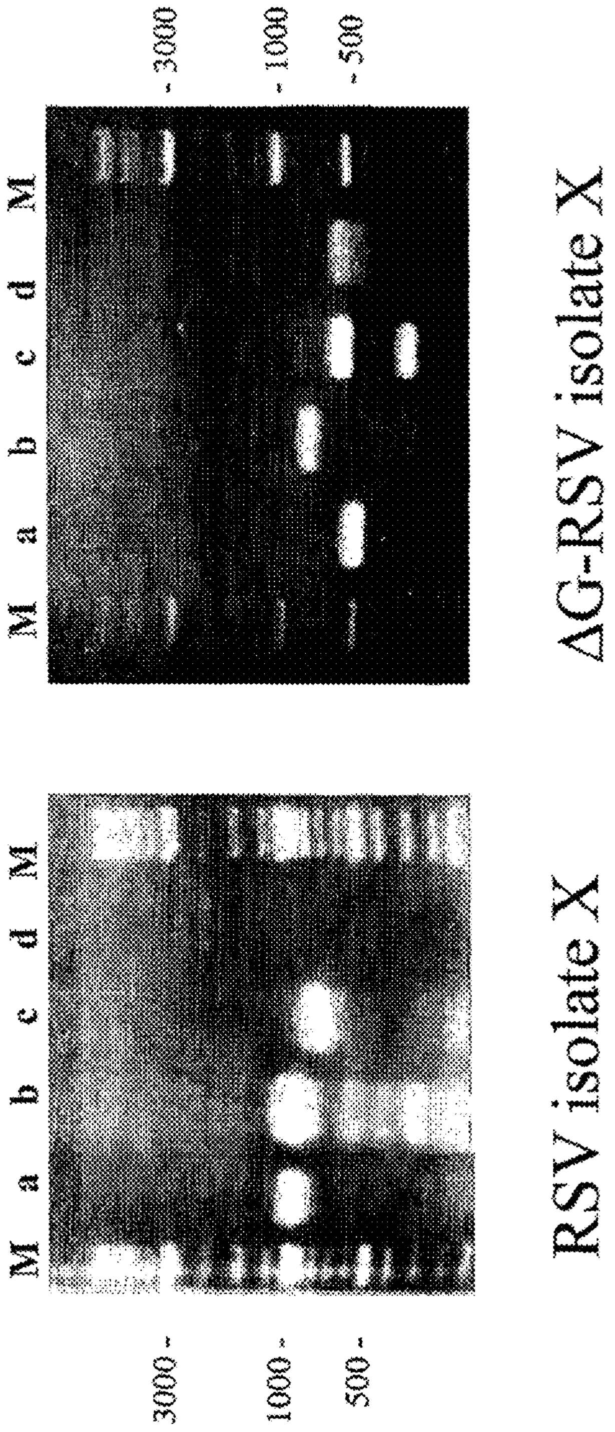

FIG. 3 Identification of sequence markers in RSV RT-PCR amplification products, digestions digests: a) MluI, b) XmaI, c) SexA-I, d) SnaB-I.

Figure 4A:
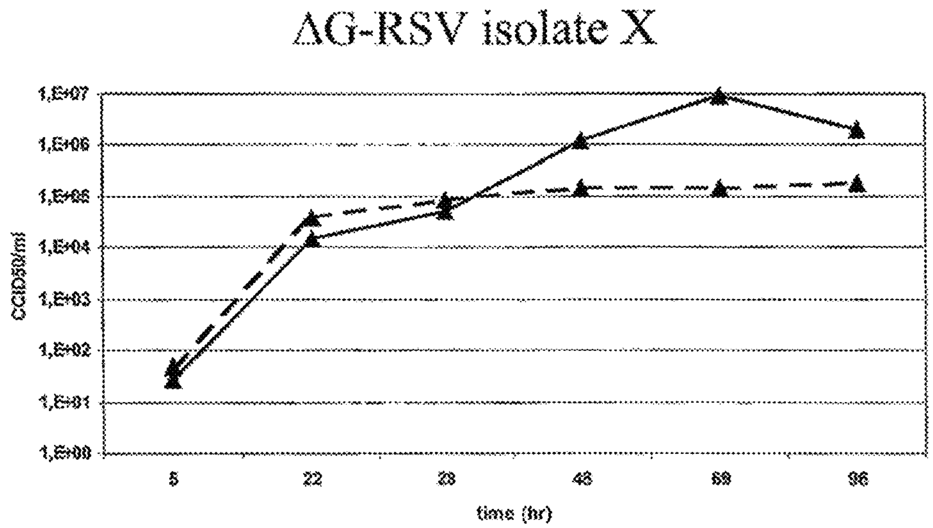
Figure 4B:
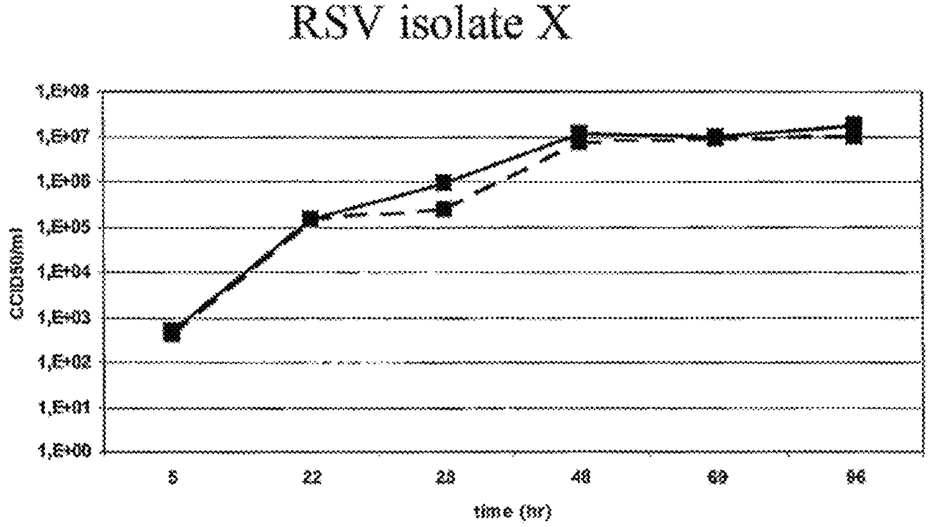

FIGS. 4A and 4B Growth curves of RSV isolate X and ΔG-RSV isolate X. Vero (solid lines) and Hep-2 (dashed lines) cells were infected with virus at MOI=0.1 and incubated at 37° C. At the indicated time points cells were harvested and CCID50 titres were determined on Vero cells.

TABLES

Table I. Primers used for RT-PCR cloning of RSV isolate X.

Table II. Primers used for cloning of helper plasmids and for plasmids used for construction of stable cell lines.

Table III. Primers used for diagnostic RT-PCR on RNA from RSV infected Vero cells.

Table IV. Results cotton rat immunization experiments, protection against RSV infection and RSV-induced pathology by ΔG-RSV isolate X immunization.

EXAMPLES

The current invention is illustrated by the following non limiting examples that are merely used to illustrate specific embodiments of the invention and should not be read as limiting the general scope or any aspect of the invention.

Example 1

Viral Isolate, Virus Isolation, Propagation and Storage

The basis for the recombinant h-RSV clone is a clinical RSV isolate, obtained from the Leiden University Medical Centre diagnostic laboratory. This virus, named 98-25147-X, coded after the patient from which it was isolated, was derived from a diagnostic test on Hep-2 cells in the period 21-24 Dec. 1998. It was later determined to be a subtype A isolate and is designated RSV isolate X. The virus was passaged 4 times on Hep-2 cells in T75 bottles in DMEM (Gibco), 10% FCS, pen/strep/glu and subsequently five times on Vero cells in T75 bottles on in DMEM (Gibco), 10% FCS, pen/strep/glu. The resulting RSV isolate X virus was used as working stock and stored at −135° C. in 25% or 45% sucrose.

Example 2

Construction of RSV-X cDNA Encoding Viral Genome

Total RNA was obtained by phenol-guanidine isothiocyanate extraction (Trizol, Invitrogen) of stock RSV isolate X infected Vero cells. cDNA was prepared by reverse transcription using Thermoscript (Invitrogen) reverse transcriptase using random hexamer primers. This cDNA was used as template for PCR using High fidelity Taq polymerase (Invitrogen) using specific primers containing restriction enzyme recognition sites (Table I and sequence listing). Primers were designed based on the published sequences of RSV-A2 (Genbank accession no M74568) and RSV-RSS2 (Genbank accession no U39662).

PCR products were first cloned individually in different vectors: primer pairs, vectors, restriction enzyme recognition sites and resulting vector name are listed below.

RSV021/RSV047: pCAP vector (Roche), bluntly into Mlu N1, pCAP3 (SH/M/P region)

RSV018/019: pCAP vector, bluntly into Mlu N1, pCAP2 (G region)

RSV016/RSV017: PUC21, Mlu I/Bam HI, pUK5 (M2-2/M2-1/F region)

RSV024/RSV025a: PUC21, Bam HI/Afl II, pUK1 (NS2/NS1 region)

RSV022/RSV023: PUC21, EcoR V, pUK4 (N region)

RSV014/RSV015: PUC21, Kpn I/Mlu I, pUK2 (L region)

At least two individual clones derived from two independent cDNA templates were sequenced; regions containing differences between the two clones were sequenced on a third clone. If necessary, clones were repaired using standard molecular biology techniques known by the skilled person. Additional PCR products covering the binding sites of the primers used for cloning were obtained and sequenced. The 5' genomic termini were determined by poly-adenylation of genomic RNA, followed by RT-PCR with an oligo(d)T containing primer ALG018 (SEQ ID NO: 34):

TTAAAAGCTTTTTTTTTTTTTTTTTTTT and an NS1 gene primer RSV126 (SEQ ID NO: 35):

```
AATTCTGCAGGCCCATCTCTAACCAAAGGAGT.
```

This fragment was cloned into pUC21 using Hind III/Pst I. The 3'-end was determined by RACE (rapid amplification of cDNA ends) ligation PCR. All sequences were assembled to yield the RSV-X consensus sequence (Seq ID No. 1).

All sequences were confirmed by PCR cycle sequencing using the BigDye terminator kit (Applied Biosystems) and analysed by an ABI Prism 310 genetic analyser.

Table I. Primers Used for RT-PCR Cloning of RSV Isolate X

TABLE I

Primers used for RT-PCR cloning of RSV isolate X

| Template region | Primer name | Sequence |
|---|---|---|
| L | RSV014 | AATTGGTACCTAATACGACTCACTATA GGGACGAGAAAAAAAGTGTC |
| | RSV015 | TTAAACGCGTCATCAAACTATTAACTC |
| M2-2/ M2-1/F | RSV016 | AATTACGCGTTAAGCATTAGGATTGA GTG |
| | RSV017 | TTAAGGATCCGCGCGCTATTATTGCAA AAAGCC |
| G | RSV018 | AATTGCGCGCTTTTTAATGACTACTGG |
| | RSV019 | TTAAGGATCCGTACGTTGGGGCAAATG CAAACATGTCC |
| SH/M/P | RSV021 | TTAACCCGGGGCAAATAAAACATCATGG |
| | RSV047 | AATTCGTACGTATTGTTAGTCTTAATATC TTAGTTCATTGTTATGA |
| N | RSV022 | AATTCCCGGGATTTTT'TTTA'TTAACTCAA AGC |
| | RSV023 | TTAAACCTGGTAAGATGAAAGATGGGGC AAATACAAAAATGGC |
| NS2/NS1 | RSV024 | AATTGGATCCACCAGGTCTCTCCTTAATT TTAAATTAC |
| | RSV025a | AATTCTTAAGGGACCGCGAGGAGGTGGA GATGCCATGCCGACCCACGCGAAAAAAT GCGTACAAC |
| HDVR | R5V026 | GTCCGACCTGGGCATCCGAAGGAGGACG |
| | RSV027 | ACGTCCTCCTTCGGATGCCCAGGTCG |
| HDVR-T7phi | RSV028 | TCGTCCACTCGGATGGCTAAGGGAATAA CCCCTTGGGGCCTCTAAACGGGTCTTGA GGGGTTTTTTGC |
| | RSV029 | GGCCGCAAAAAACCCCTCAAGACCCGTT TAGAGGCCCCAAGGGGTTATTCCCTTAG CCATCCGAGTGGACG |

Example 3

Construction of ΔG-RSV Isolate X Full Length Plasmid

Figure 1:
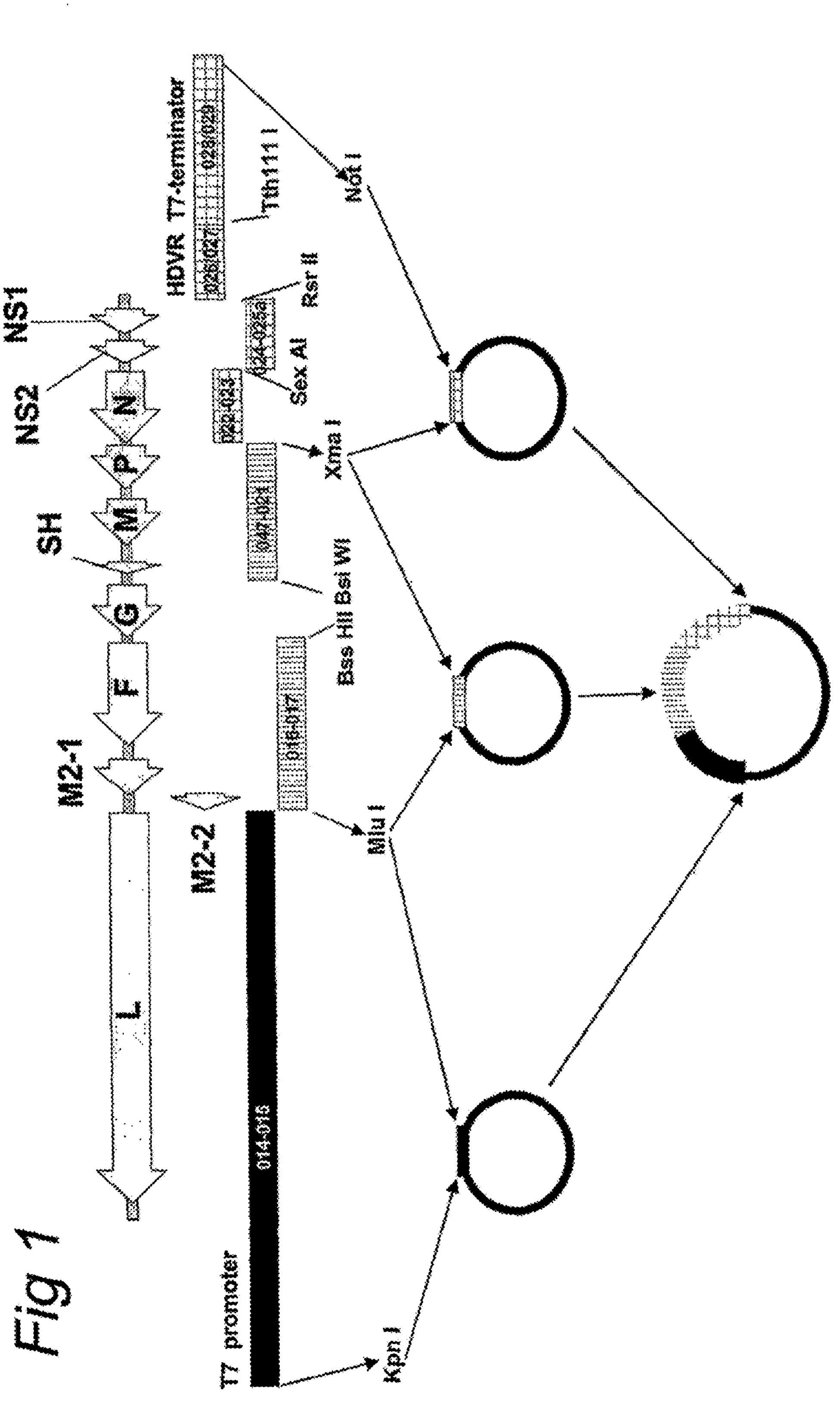
FIG. 1 Diagram of construction of pRSVXΔG. Upper line represents RSV isolate X genomic RNA, with genes indicated. Boxes below represent RT-PCR products and oligonucleotide duplexes used for construction. Numbers inside boxes indicate the oligonucleotide numbers as listed in table I. Restriction sites introduced for cloning are indicated. The final cloning scheme is indicated below: circles are plasmids and the arrows show the order of cloning.

The full-length cDNA spanning the entire RSV isolate X genome was assembled by sequential ligation of PCR fragments (FIG. 1). The "trailer" end is preceded by the promoter for the bacteriophage T7 polymerase. To generate correct 3' ends the cDNA "leader" end is fused to the hepatitis delta virus ribozyme (HDVR), followed by a terminator of the T7 RNA polymerase transcription (see FIG. 1).

First, two sets of complementary oligomers encoding the HDVR and the T7 terminator RSV026/RSV027 oligo's and RSV028/029 oligo's were phosphorylated with T4 DNA kinase, hybridised and ligated into clone pUK1 (containing genes NS1/NS2) via Rsr II/Not I, giving plasmid pUK3. Then, the Xma I/SexA I fragment of clone pUK4 containing N was ligated into plasmid pUK3 via Xma I/SexA I. This plasmid (pUK6) contains the region from the N gene up to the 3' leader sequence, fused to the HDVR and a T7 terminator.

Secondly, the Xma I/Eco RV fragment of plasmid pCAP3 was inserted in plasmid pUK5 using Xma I and a filled-in Hind III site. This yields plasmid pUK8. Subsequently, pUK 8 was digested with BssH II and BsiW I, ends were filled-in with Klenow polymerase and religated. This plasmid contains the genes M2-2, M2-1, F, SH, M and P and is named pUK9.

To synthesise a low-copy number vector for the RSV isolate X cDNA, two complementary oligomers,

```
                                        (SEQ ID NO: 36)
RSV011:
AGCTTGCGGCCGCGTCGACCCGGGACGCGTCGATCGGGTACCAT
and
                                        (SEQ ID NO: 37)
RSV012:
CGATGGTACCCGATCGACGCGTCCCGGGTCGACGCGGCCGCA
```

were phosphorylated with T4 DNA kinase, hybridised and inserted in the alkaline phosphatase treated and Cla I/Hind III digested plasmid pACYC184 (New England Biolabs). The resulting plasmid is named pACYC184-MCS. Subsequently a Mlu I-Knp I fragment of pUK2 containing the T7 promoter and L gene was inserted, this intermediate plasmid is named pACYC1. Then, the region from the N gene up to the 3'-leader sequence, including the fused HDVR and T7 terminator sequence of pUK6 was added to pACYC1 using Xma I/Not I. This gives intermediate plasmid pACYC2. Finally, the Xma I/Mlu I fragment of pUK9 containing the M2-2, M2-1, F, SH, M and P genes was inserted into pACYC2, yielding plasmid pACYC3, comprising the whole RSV genome of strain X lacking the G gene. Sequence analysis of the latter plasmid revealed a deletion in the HDVR region, which was repaired and the resulting plasmid is named pRSVXΔG.

In addition to construct pRSVXΔG, construct pACYC24 was generated in which the genomic RSV isolate X insert is reverse complemented via inverse PCR. From the construct, antigenomic RSV RNA can be synthesised. In pACYC24, the T7 promoter precedes the 3'-leader sequence, whereas the HDVR and T7 terminator are fused to the 5'-trailer sequence.

Figure 2A:
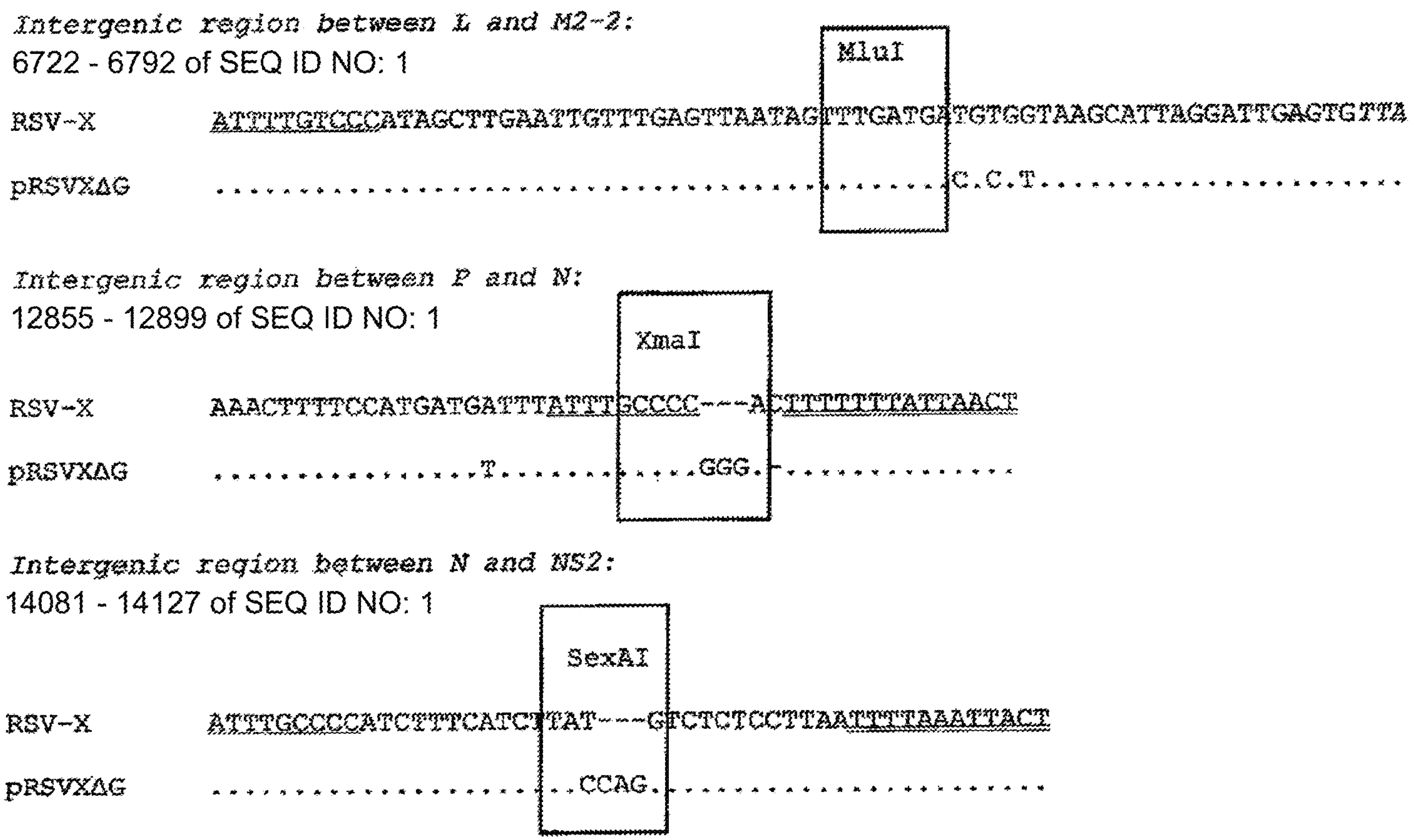
FIGS. 2A and 2B Alignments showing the differences between RSV isolate X and pRSVXΔG sequences. Sequences are shown as alignment of genomic sense. For pRSVXΔG only nucleotides differing from RSV isolate X are indicated. Similar sequences are indicated by dots (.) and gaps are indicated by (-). Gene start signals are single underlined, gene stop signals double underlined, and the genes are indicated in the captions. Boxes outline the restriction enzyme recognition sites resulting from the nucleotide changes introduced. The sequences presented in FIGS. 2A and 2B correspond with the following fragments of SEQ ID NO: 1.
Figure 2B:
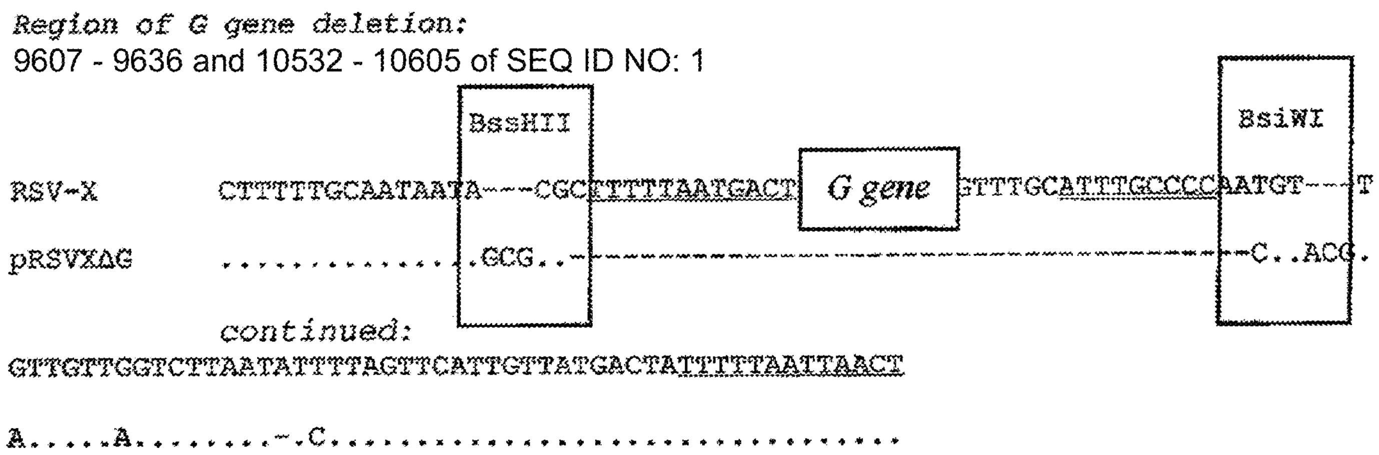

All restriction enzyme recognition sites used to construct pRSVXΔG are located inside the RSV intergenic regions and do not alter coding sequences or affect transcription signals (as shown in FIGS. 2A and 2B).

Example 4

Construction of Helper Plasmids

Helper plasmids expressing several RSV proteins were constructed as follows. All required genes are derived from lab-strain RSV-A2 (ATCC #VR1302). Virus was plaque-purified on Hep-2 cells and subsequently used to infect Vero cells. Total RNA was isolated from these cells by phenol-guanidine isothiocyanate extraction (Trizol, Invitrogen) and subjected to RT-PCR using High Fidelity Taq polymerase (Invitrogen) and a set of primers specific for RSV genes L, P, N and M2-1 respectively (see Table II). PCR products were subsequently cloned into expression plasmids pcDNA3, pcDNA6 or pCI, using restriction enzyme recognition sites as indicated in the table II. Clone sequences were confirmed by PCR cycle sequencing using the BigDye terminator kit (Applied Biosystems) and analysed by an ABI Prism 310 genetic analyser.

Table II. Primers Used for Cloning of Helper Plasmids and for Plasmids Used for Construction of Stable Cell Lines.

TABLE II

Primers used for cloning of helper plasmids and for plasmids used for construction of stable cell lines.

| Gene | Primer name | Sequence | Restriction sites |
|---|---|---|---|
| L | RSV045 | TTAACTCGAGTTATTCATTATGA AAGTTG | Xho I |
| | RSV046 | AATTGGTACCGGGACAAAATGG ATCCC | Kpn I |
| P | RSV043 | TTAATCTAGATTGTAACTATATT ATAG | Xba I |
| | RSV012a | AATTGGATCCGGGGCAAATAAAT CATCATGG | BamH I |
| N | RSV010 A | AATTGGATCCGGGGCAAATACA AGATGGC | BamH I |
| | RSV011 | TTAACTCGAGATTAACTCAAAGC TCTACATC | Xho I |
| M2-1 | RSV124 | AATTGGATCCGGGGCAAATATGT CACGAAGG | BamH I |
| | RSV125 | TTAATCTAGATCAGGTAGTATCA TTATTTTTGGC | Xba I |
| A2-G | RSV042 | TTAATCTAGAAGTAACTACTGGC GTG | Xba I |
| | RSV004a | AATTGGATCCGGGGCAAATACA AACATGTCCAAAAACAAGGACC | BamH I |
| | RSV151 | AATTCCATGGGGTCCAAAACCAA GGACCAACG | Nco I |
| A2-GΔM48 | RSV033a | AAAAGTATACTTAATGTGATTTG TGCTATAG | Acc I |
| | RSV034 | TTTTGTATACTGGCAGCTATAAT CTCAACTTCACTTATAATTGC | Acc I |
| X-G | RSV004a | AATTGGATCCGGGGCAAATACA AACATGTCCAAAAACAAGGACC | BamH I |
| | RSV018a | AATTTCTAGATTTTTAATGACTA CTGG | Xba I |
| T7 pol | ALG022 | TTAATCTAGACGTTACGCGAACG CGAAGTCC | Xba I |
| | ALG023 | AATTAAGCTTACCATGGACACGA TTAACATCGCTAAGAACG | Hind III |

Example 5

Construction of G-Producing Vero Cell-Lines

Cell lines producing RSV-G protein were constructed using several methods:

In method 1, the G gene from either RSV-A2 or RSV isolate X, or the G gene from RSV-A2, in which the internal translation initiation codon had been disabled by modification using primers RSV033 and RSV 034, were cloned into expression vector pcDNA3 or pcDNA6 (Invitrogen) using RT-PCR on RNA from RSV-A2 or RSV isolate X infected Vero cells using primers as indicated in Table II. The plasmids were introduced into Vero cells using either chemical agents $CaCl_2$, co-precipitation, liposome-based or electroporation (Ausubel 1989). Two methods for isolating stable cell lines were used. In the first method, 72 hours after transfection, cells were split using various dilutions into fresh medium containing selective medium, zeocin for pcDNA3 and blasticidin for pcDNA6. Cells were fed with selective medium every 3-4 days until cell foci were identified. Single colonies were picked and transferred in to 96-well plate, or seeded in various dilutions to obtain single cells in a 96 well plate. Antibiotic resistant colonies were tested on expression of RSV-G by immunostaining techniques or FACS using RSV G-specific antibodies. Colonies expressing G were passaged, and were designated as stable cell lines expressing G. The second method comprises FACS sorting using RSV-G specific antibodies 72 hours after transfection. RSV-G expressing cells were seeded in a serial dilution to obtain single cells in a 96-well plate and cultured with selective medium. Single cell colonies were passaged on selective medium and subsequently tested again for expression of RSV-G, resulting in cell lines expressing RSV-G.

In method 2, the Flp-In system (Invitrogen) is used to produce Vero cells with target gene insertion sites at chromosomal positions which allow different levels of target gene expression. The RSV-G gene, derived from the plasmids from method 1 but with a modification (introduced using primer RSV151: Table II) of the G translation initiation codon surrounding sequence to allow higher translation levels, were inserted in each of these cell lines using the system-generic method, resulting in Vero cell lines stably expressing different levels of G protein.

In method 3, Vero cells were transiently made to express the G protein, by either transfection with the expression plasmids containing the G gene from method 1, or by infection with Modified vaccinia virus Ankara (MVA) (Sutter 1992) or fowlpox viruses (Spehner 1990) expressing the G protein.

Example 6

Construction of Bacteriophage T7-Polymerase-Producing Cell Lines

The bacteriophage T7 polymerase gene is PCR amplified from plasmid pPRT7 (van Gennip 1997), containing the gene, using primers ALG022 and ALG023 (Table II). The PCR product is cloned into pcDNA6b vector, using Hind III/Xba I, yielding plasmid pc6T7pol. Vero cells were transfected using lipofectamine 2000 as recommended by the manufacturer (Invitrogen). 72 hours after transfection cells were split and grown in fresh medium containing blasticidin. Cells were fed fresh medium every 3-4 days and split twice to obtain larger culture volumes. 20 days after transfection, blasticidin resistant cells were transfected with reporter plasmid pT7-IRES2-EGFP using lipofectamine 2000. For the construction of plasmid pT7-IRES2-EGFP, first plasmid pT7-EGFP was constructed by inserting via HindIII/BamH1 in plasmid p-EGFP-N1 (Clonetech) a set of complementary oligomers encoding for the T7 promoter sequence (ALG32 (SEQ ID NO: 38): AGCTAATACGACTCACTATAGGGA-GACGCGT and ALG33 (SEQ ID NO: 39): GAT-CACGCGTCTCCCTATAGTGAGTCGTATT). Plasmid pT7-IRES2-EGFP was then constructed by cloning the T7-EGFP fragment of plasmid pT7-EGFP into plasmid p-IRES2-EGFP via Xma1-Not1. Cells expressing EGFP were sorted by FACS and grown in limited dilution to obtain single cell colonies. Single colonies expressing T7 RNA polymerase were tested for stability, grown to larger culture volumes and stored.

Example 7

Method to Produce Recombinant ΔG-RSV Isolate X Virus

Hep-2 cells were cultivated in DMEM+10% FCS (foetal calf serum)+penicillin/streptomycin/glutamine, whereas Vero cells and derivatives thereof are cultivated in M199+ 5% FCS+pen/strep/glu. Cells were grown overnight to 80% confluence in 10 $mm^2$ dishes at 37° C. For Vero and Hep-2 cells, cells were infected with modified virus Ankara-T7 (MVA-T7)(Sutter 1992, Wyatt 1995) or fowlpox-T7 virus (Britton 1996) at MOI=3 (multiplicity of infection 3) and incubated at 32° C. for 60 min prior to transfection, to allow expression of bacteriophage T7 polymerase. The cells (Hep-2, Vero or Vero-T7 cells) were washed with Optimem medium (Optimem 1 with glutamax, Invitrogen) and subsequently transfected with helper plasmids encoding the N, P, L and M2.1 genes of RSV and with plasmid pRSVXΔG, using Lipofectamine 2000 (Invitrogen) in Optimem (total volume 500 μl). The following amounts of plasmids were added: 1.6 μg pRSVXΔG, 1.6 μg pcDNA6-A2-N, 1.2 μg pcDNA3-P, 0.4 μg pcDNA6-A2-L, 0.8 μg pcDNA6-A2-M2.1. After 3-4 hrs of incubation at 32° C., 500 μl of Optimem medium with 2% FCS was added and the cells were incubated at 32° C. for 3 days. Cells were then scraped and the mixture of scraped cells and medium containing the rescued virus was used to infect fresh cultures of Vero or Hep-2 cells grown in DMEM+2% FCS+pen/strep/glu. The latter procedure was repeated for 4-5 times to obtain high titre virus stocks.

Identity of ΔG-RSV isolate X virus was confirmed by RT-PCR on RNA isolated from ΔG-RSV isolate X infected Vero cells and digestion of the obtained products with the unique restriction enzymes whose recognition sites were introduced into pRSVXΔG (FIGS. 2A and 2B). RSV isolate X was used as control.

For the identification of sequence markers in RSV, Vero cells were infected with RSV isolate X or with ΔG-RSV isolate X with an MOI=0.1. 72 hrs after infection, RNA from culture supernatants was isolated and used as template for RT-PCR. Primers were designed to flank the inserted sequence markers in the recombinant ΔG-RSV isolate X virus. After RT-PCR, the obtained products were digested with the appropriate restriction enzymes. The following digestion products were obtained (FIG. 3):

a) PCR with primer RSV065 (SEQ ID NO: 40) (GTCCATTGTTGGATTTAATC) and RSV093 (SEQ ID NO: 41) (CAAGATAAGAGTGTACAATACTGTC) and digestion with Mlu-I yielded the expected fragments of 937 bp for RSV isolate X, and 459 and 478 bp for ΔG-RSV isolate X b) PCR with primers RSV105 (SEQ ID NO: 42) (GTTGGATTGAGAGACACTT) and RSV113 (SEQ ID NO: 43) (AGTATTAGGCAATGCTGC) followed by digestion with Xma-I yielded the expected fragments of 880 bp for RSV isolate X, and 656 and 224 bp for ΔG-RSV isolate X c) PCR with primers RSV112 (SEQ ID NO:44) (CCCAGTGAATTTATGATTAG) and RSV160 (SEQ ID NO:45) (AATTGGATCCATGGACACAACCCACAATGA) and digestion with SexA-I yielded the expected fragments of 694 bp for RSV isolate X, and 492 and 202 bp for ΔG-RSV isolate X d) PCR with primers RSV098 (SEQ ID NO:46) (TGGTAGTTCTCTTCTGGCTCG) and RSV114 (SEQ ID NO:47) (ATCCCCAAGTCATTGTTCA) followed by digestion with SnaB-I yielded the expected fragments of 1820 bp for RSV isolate X, and 507 and 387 bp for ΔG-RSV isolate X.

Growth characteristics of ΔG-RSV isolate X compared to RSV isolate X were determined on Vero and on Hep-2 cells (FIGS. 4A and 4B).

TABLE III

Primers used for diagnostic RT-PCR on RNA from RSV infected Vero cells.

| Primer name | Sequence | SEQ ID NO: |
|---|---|---|
| RSV065 | GTCCATTGTTGGATTTAATC | 40 |
| RSV093 | CAAGATAAGAGTGTACAATACTGTC | 41 |
| RSV098 | TGGTAGTTCTCTTCTGGCTCG | 46 |
| RSV105 | GTTGGATTGAGAGACACTT | 42 |
| RSV112 | CCCAGTGAATTTATGATTAG | 44 |
| RSV113 | AGTATTAGGCAATGCTGC | 43 |
| RSV114 | ATCCCCAAGTCATTGTTCA | 47 |
| RSV160 | AATTGGATCCATGGACACAACCCACAATGA | 45 |

Example 8

Method to Produce Recombinant ΔG+G-RSV Isolate X Virus

ΔG-RSV isolate X virus, derived from transfected Vero cells, was passaged several times to obtain titres of at least $10^5$ pfu/ml (plaqrsv045ue forming units per ml). Different moi's of this virus were then used to infect the Vero cell line producing RSV-G protein. The resulting ΔG+G-RSV isolate X was harvested from the medium and/or from the cells and analysed for the presence of the G protein in the virions by immunodetection techniques. Infectivity titres were determined on Vero or Hep-2 cells, and the integrity of the ΔG-genome was determined using RT-PCR on viral RNA extracted from cells infected with ΔG+G-RSV isolate X virus. Virus was stored at −135° C. in 25% or 40% sucrose.

Example 9

Method to Protect in a Cotton Rat Animal Model Against RSV Infection and RSV-Induced Pathology by ΔG-RSV Isolate X Immunization Protection experiments were performed in cotton rats (*Sigmodon hispidus,* 5-6 weeks old, 4-6 animals per group and both sexes). In initial experiments, this animal was shown to be sensitive to RSV infection and to exhibit severe vaccine-mediated lung pathology as described by Prince, 2001 and which closely mimics the human situation. After intranasal application of RSV lung pathology was characterized by inflammation infiltrate in and around bronchus/bronchioli and hyperplasia of epithelium. A more severe pathology was seen upon intramuscular immunization with formalin-inactivated RSV-A2 followed by an intranasal challenge with RSV-A2. In addition to the above-mentioned pathology, perivascular and peribronchiolar infiltrate and alveolitis were observed, characteristic for an immune-mediated pathology. These observations were used as "internal" reference for all immunization and challenge experiments. Infection and immunization of cotton rats with RSV preparations was done intranasally, in both nostrils. Cotton rat lungs were examined for pathology lightmicroscopically and virus titres at different time points post-challenge or post-infection/immunization were determined on Vero cells using serial dilutions of lung homogenates with RSV specific ELISA to yield $CCID_{50}$ titres and immunostaining using RSV specific abs to yield pfu titres. After immunization twice with ΔG-RSV isolate X cotton rats were fully protected against infection and pathology caused by RSV isolate X in the lungs. The results from several experiments are summarized in Table IV.

TABLE IV

| infection with: | t[1] | V[2] | lung pathology day 5 post infection | lung t[3] |
|---|---|---|---|---|
| ΔG-RSV isolate X | 5 | 100 | yes, moderate | below detection |
| RSV-A2 | 5 | 100 | yes, strong | 2*5 |
| RSV isolate X | 5 | 100 | yes, strong | 4*5 |

| immunization day 0 and 21 | t[1] | V[2] | challenge day 42 | t[1] | V[2] | lung pathology day 5 post challenge | lung t[3] |
|---|---|---|---|---|---|---|---|
| 2x ΔG-RSV isolate X | 5 | 100 | RSV isolate X | 5 | 100 | no | below detection |
| mock | | 100 | RSV isolate X | 5 | 100 | yes, strong | 5 |

[1]virus titres in logs pfu/ml
[2]volume in μl per animal, which is half this volume in each nostril
[3]virus titres in logs per gram lung, detection limit is $10^2$ $CCID_{50}$

REFERENCES

Alwan W H, Record F M, Openshaw P J. Phenotypic and functional characterisation of T cell lines specific for individual respiratory syncytial virus proteins. J Immunol. 1993, 150(12):5211-8.

F. M. Ausubel, R. Brent, R. E. Kingston, D. D. Moore, J. G. Seidman, J. A. Smith, K. Struhl, Current Protocols in Molecular Biology, John Wiley and Sons, New York, 1997

Bembridge G P, Rodriguez N, Garcia-Beato R, Nicolson C, Melero J A, Taylor G. DNA encoding the attachment (G) or fusion (F) protein of respiratory syncytial virus induces protection in the absence of pulmonary inflammation. J Gen Virol. 2000, 81 (Pt 10):2519-23.

Britton P, Green P, Kottier S, Mawditt K L, Penzes Z, Cavanagh D, Skinner M A. Expression of bacteriophage T7 RNA polymerase in avian and mammalian cells by a recombinant fowlpox virus. J Gen Virol. 1996, 77 (Pt 5):963-7.

Buchholz U J, Granzow H, Schuldt K, Whitehead S S, Murphy B R, Collins P L. Chimeric bovine respiratory syncytial virus with glycoprotein gene substitutions from human respiratory syncytial virus (HRSV): effects on host range and evaluation as a live-attenuated HRSV vaccine. J Virol. 2000, 74(3):1187-99.

Cane P A, Matthews D A, Pringle C R. Identification of variable domains of the attachment (G) protein of subgroup A respiratory syncytial viruses. J Gen Virol. 1991, 72 (Pt 9):2091-6.

Collins P L, Purcell R H, London W T, Lawrence L A, Chanock R M, Murphy B R. Evaluation in chimpanzees of vaccinia virus recombinants that express the surface glycoproteins of human respiratory syncytial virus. Vaccine. 1990, 8(2):164-8

Crowe J E Jr. Immune responses of infants to infection with respiratory viruses and live attenuated respiratory virus candidate vaccines. Vaccine. 1998, 16(14-15):1423-32. Review.

Gonzalez I M, Karron R A, Eichelberger M, Walsh E E, Delagarza V W, Bennett R, Chanock R M, Murphy B R, Clements-Mann M L, Falsey A R. Evaluation of the live attenuated cpts 248/404 RSV vaccine in combination with a subunit RSV vaccine (PFP-2) in healthy young and older adults. Vaccine. 2000, 18(17):1763-72.

Greenough A, Thomas M. Respiratory syncytial virus prevention: past and present strategies. Expert Opin Pharmacother. 2000, 1(6):1195-201.

Jin H, Cheng X, Traina-Dorge V L, Park H J, Zhou H, Soike K, Kemble G. Evaluation of recombinant respiratory syncytial virus gene deletion mutants in African green monkeys for their potential as live attenuated vaccine candidates. Vaccine. 2003, 21(25-26):3647-52.

Karron R A, Buonagurio D A, Georgiu A F, Whitehead S S, Adamus J E, Clements-Mann M L, Harris D O, Randolph V B, Udem S A, Murphy B R, Sidhu M S. Respiratory syncytial virus (RSV) SH and G proteins are not essential for viral replication in vitro: clinical evaluation and molecular characterisation of a cold-passaged, attenuated RSV subgroup B mutant. Proc Natl Acad Sci USA. 1997, 94(25):13961-6.

Kim H W, Canchola J G, Brandt C D, Pyles G, Chanock R M, Jensen K, Parrott R H. Respiratory syncytial virus disease in infants despite prior administration of antigenic inactivated vaccine. Am J Epidemiol. 1969, 89(4):422-34.

Li X, Sambhara S, Li C X, Ewasyshyn M, Parrington M, Caterini J, James O, Cates G, Du R P, Klein M. Protection against respiratory syncytial virus infection by DNA immunization. J Exp Med. 1998, 188(4):681-8.

Lofland J H, O'Connor J P, Chatterton M L, Moxey E D, Paddock L E, Nash D B, Desai S A. Palivizumab for respiratory syncytial virus prophylaxis in high-risk infants: a cost-effectiveness analysis. Clin Ther. 2000, 22(11):1357-69.

Mufson M A, Belshe R B, Orvell C, Norrby E. Respiratory syncytial virus epidemics: variable dominance of subgroups A and B strains among children, 1981-1986. J Infect Dis. 1988, 157(1):143-8.

Neumann G, Whitt M A, Kawaoka Y. A decade after the generation of a negative-sense RNA virus from cloned cDNA—what have we learned? J Gen Virol. 2002, 83(Pt 11):2635-62. Review.

Openshaw P J, Dean G S, Culley F J. Links between respiratory syncytial virus bronchiolitis and childhood asthma: clinical and research approaches. Pediatr Infect Dis J. 2003, 22(2 Suppl):S58-64; discussion S64-5. Review.

Peebles R S Jr, Hashimoto K, Graham B S. The complex relationship between respiratory syncytial virus and allergy in lung disease. Viral Immunol. 2003; 16(1):25-34. Review.

Plotnicky H, Siegrist C A, Aubry J P, Bonnefoy J Y, Corvaia N, Nguyen T N, Power U F. Enhanced pulmonary immunopathology following neonatal priming with formalin-inactivated respiratory syncytial virus but not with the BBG2NA vaccine candidate. Vaccine. 2003, 21(19-20): 2651-60.

Power U F, Plotnicky-Gilquin H, Huss T, Robert A, Trudel M, Stahl S, Uhlen M, Nguyen T N, Binz H. Induction of protective immunity in rodents by vaccination with a prokaryotically expressed recombinant fusion protein containing a respiratory syncytial virus G protein fragment. Virology. 1997, 230(2):155-66.

Prince G A, Curtis S J, Yim K C, Porter D D. Vaccine-enhanced respiratory syncytial virus disease in cotton rats following immunization with Lot 100 or a newly prepared reference vaccine. J Gen Virol. 2001, 82:2881-8.

Robinson R F, Nahata M C. Respiratory syncytial virus (RSV) immune globulin and palivizumab for prevention of RSV infection. Am J Health Syst Pharm. 2000, 57(3): 259-64. Review. Erratum in: Am J Health Syst Pharm 2000 Apr. 1; 57(7):699.

Sambrook J., Fritsch E F, Maniatis T. Molecular Cloning. A Laboratory Manual, 2nd ed. Cold Spring Harbor Laboratory Press, Cold Spring Harbor, N.Y., 1989

Schmidt U, Beyer J, Polster U, Gershwin L J, Buchholz U J. Mucosal immunization with live recombinant bovine respiratory syncytial virus (BRSV) and recombinant BRSV lacking the envelope glycoprotein G protects against challenge with wild-type BRSV. J Virol. 2002, 76(23):12355-9.

Siegrist C A, Plotnicky-Gilquin H, Cordova M, Berney M, Bonnefoy J Y, Nguyen T N, Lambert P H, Power U F. Protective efficacy against respiratory syncytial virus following murine neonatal immunization with BBG2Na vaccine: influence of adjuvants and maternal antibodies. J Infect Dis. 1999, 179(6):1326-33.

Spehner D, Drillien R, Lecocq J P. Construction of fowlpox virus vectors with intergenic insertions: expression of the beta-galactosidase gene and the measles virus fusion gene. J Virol. 1990, 64(2):527-33.

Srikiatkhachorn A, Braciale T J. Virus-specific CD8+T lymphocytes downregulate T helper cell type 2 cytokine secretion and pulmonary eosinophilia during experimental murine respiratory syncytial virus infection. J Exp Med. 1997a, 186(3):421-32.

Srikiatkhachorn A, Braciale T J. Virus-specific memory and effector T lymphocytes exhibit different cytokine responses to antigens during experimental murine respiratory syncytial virus infection. J Virol. 1997b, 71(1):678-85.

Sutter G, Moss B. Nonreplicating vaccinia vector efficiently expresses recombinant genes. Proc Natl Acad Sci USA. 1992, 89(22):10847-51.

Van Gennip H G, van Rijn P A, Widjojoatmodjo M N, Moormann R J. Recovery of infectious classical swine fever virus (CSFV) from full-length genomic cDNA clones by a swine kidney cell line expressing bacteriophage T7 RNA polymerase. J Virol Methods. 1999, 78(1-2):117-28.

Wyatt L S, Moss B, Rozenblatt S. Replication-deficient vaccinia virus encoding bacteriophage T7 RNA polymerase for transient gene expression in mammalian cells. Virology. 1995, 210(1):202-5.

The invention claimed is:

1. A vaccine composition consisting essentially of:

(a) a virion of a human Respiratory Syncytial Virus comprising a viral genome that has an inactivating mutation in only the gene coding for a G attachment protein;

(b) an adjuvant; and, optionally, (c) a pharmaceutically acceptable excipient selected from the group consisting of carriers, stabilisers, solubilisers, and preservatives.

2. The vaccine composition of claim 1, wherein the inactivating mutation comprises a deletion of the entire sequence coding for the G attachment protein from the viral genome.

3. The vaccine composition according to claim 1, wherein the carrier is selected from water, buffered saline solutions, glycerin, polysorbate 20, cremophor EL, and an aqueous mixture of caprylic/capric glyceride.

* * * * *

SEQUENCE LISTING

```
<160> NUMBER OF SEQ ID NOS: 47

<210> SEQ ID NO 1
<211> LENGTH: 15213
<212> TYPE: DNA
<213> ORGANISM: Human respiratory syncytial virus

<400> SEQUENCE: 1

acgagaaaaa aagtgtcaaa aactaatatc tcgtagttta gttaatatac atataaacca      60

attagatttg ggtttaaatt tattcctcct agatcaaaat gataatttta ggattagttc     120

actagaagtt attaaaaatt atataattat taattttaaa taactataat tgaatacagt     180

gttagtgtgt agccatggga atttttatta taagattttt gttcattatt cattatggaa     240

gttgtataac aaactacctg tgattttaat cagtttttta agttcattgg ttgtcaagct     300

gtttaacaat tcacttagat gaggatatgt agattctacc atatataaat gattatagtt     360

taattctgtt gatctgaaat ttaaaacatg attgaaccac tttaagatgt tcatgtgctt     420

atgatttata agtttattgc tgaaaacttc attacgtcca gctatagaat aagatagtat     480

atctccacta acaacactct ttagtttaga caatgcagta ttaattcctt tttttgttat     540

agggtaacaa agaaagggta tcaaactctt aatatttgca tcaatagact ctttatcagc     600

cttcttaggc atgatgaaat ttttggttct tgatagtatc aatttagcat tttgtactac     660

attaaatact gggaacacat ttgcaggacc tattgtaagg actaagtaaa cttcagatcc     720

ctttaactta ctgcctaagc atacataagt ttttaatata gttatgttgt ctaatttgaa     780

atcgatatca tcttgagcat gatattttac tattaacgta catttattaa ctgaagaaca     840
```

-continued

```
gtacttgcat tttcttacat gcttgctcca ctctattata attttattcc agttgactgt    900
tacaggcaat tcagcatcac agacaaaaag gctgataggt tcagcaaact ttatatgtaa    960
ataagaccaa tgaatgttgt tggttgcatc tgtagcagga atggtcaaat tttcaccata   1020
atcaatgttg atatgtccat tgtacagcct taaaaactca attggtaaac tatgatcatt   1080
acaatctttc agacttctgt aaatatatct tatatcagga tgaagttcca ctactgtacg   1140
caataataaa ttccctgctc cttcacctat gaatgctata caattaggat ctttaatttt   1200
aaggtctttt aaaatatact ctatactaat tttacaacct gtagaactaa atacaaaatt   1260
gaatctatta atatgatgcc aaggaagcat gcaataaagt gatgtgctat tgtgtactaa   1320
agatatttga tgagaagtag tagtgtaaag ttggttagat ttggctgtat tacctgaatg   1380
atctataatt ttatcaatca caaccgtagg aaataaatta tacaaatctt gtctgctgta   1440
attggttcta atcattgtag acgatttaat aagcttctta ttagataaca atggtaacat   1500
tattgagtca acatttttac ctatacaata gtcattcagt gtctttttat cattactttt   1560
aaccggattg gttagtatat tttctagggt ttctggtgta ggatgatata atttgttgta   1620
attactttct aattcagaat tagcaatcct tatatgttta gttaatagat gagtattatc   1680
tgagaagtta taattaatgt aaaaaagatt agaagtataa aattcatcat tgaatttgtg   1740
tttattttta atgtatattc tatctatatt tatcaatccc attctaacaa gatctatata   1800
agttaatatt gctttcatat gtgttggatg ataatctatg ttaacaaccc aagggcaaac   1860
tgtgaattct gctacattaa gacgtttaag aaaccatagt ttgaagctat gacatccttt   1920
tactctatgt aaacttgcat cctggctaag aatgtatttg ataacttttt gttctaaaaa   1980
taccttagac atagacttcc aataactact gtctattaat tccaatacac ataggagatc   2040
tgaagtattc atatcacact ccagctttgc tctgctgtaa cctttatgaa aacacaagag   2100
atatgtctta taagcattga agaaaacttt caaattaatg aacatatgat cagttatata   2160
tccctctccc caatcttttt caaaaatacc tttagaatct ttcataagtt gtataatcag   2220
aatccaatgt ccagctaaat tagtacttaa aatgtaagta ttatgaaaat agtcagatat   2280
cttatgcgcc aatattaaat tagaattaac attagatcca gattttagtg ttttattact   2340
taagaataat tccacatatt gagtcaaact tattttgtct ggtaaaaaca tatgctgttt   2400
ttgtatcact tgttttaact tgtgaatatc aacatcacct gtgaatatgg gaggtttcat   2460
caaatgtatc tcattaagct tgggtatgag aataattctg ttaggacata cattagtaaa   2520
ttgttctact actgacatta agctaaggcc aaagcttata cagttttgga atactatatc   2580
aatatcttca tcaccatact tttctgttaa tatgcgatta atagggctag tatcaaagtg   2640
atagtttgta gttctatagg ctggtattga tgcagggaat tcacatggtc tactactgac   2700
tgtaagacga tgcaaatagt taacacttaa atattgtgga aataattttt tggccttctc   2760
atatgctaac ccaagagttc ctatgctaag ttcctccatg aattcatcct tgttatctat   2820
agatgcatac acccaatcca attttgctaa tagatctatt tgatctctct gttttttggt   2880
taaaacttgt ctattataaa ctggcattgt ttttttctct tgtgtagatg aaccaaccca   2940
tggtttagtg ggtcctctct caccacgtgt taaactgttg acattatatt tctctatgat   3000
tatgccacta gctatagtgc ttgttgtata tttgatgtcc attgtataca tgatactggg   3060
tgatgtaaca ccaactatat tggataaaga ccaagatctt tctctaacat atttacttaa   3120
ttcagtaata cttaggtttt ccatactcaa tatttctctt ttatctctgt tacaatctaa   3180
tggtaatatc cttataagca aagttatgtt tttcctcatc atctcagtgg ctctatcaat   3240
```

-continued

```
atctgttaag tctatggcag aagtcttttc cagtatgtta gttatagatt ttgtaccgga   3300
tataagattt actattttct ctgctttata aaagggtaaa ctttcataaa caactcttag   3360
cccgtgagga tatgtaggtt ctatattttg cataatatca ttaagatcta tctctgtagt   3420
ggtatagtgt tgtgcacttt tggagaatat tttgtttgga gctgtgctca aaacctcagt   3480
aactgccagt ctattgattt cactagtaat tttagcttgc ctctcagatc ctaaagcttg   3540
aggatctctc atcaatgtta caaattcagc attagggttt ttgtcaaacg tgattatgca   3600
tgttaagaat ttattcaatc tatcatctga cagatcttga agtttatctt ttaaatcatg   3660
gtttgtataa taactaagta tgaacacaga gtgaactata gcctctgtga gaaaatcagg   3720
agttcttcta tagaaacttc gatataacaa gttgggatca ccaccaccaa ataacatggg   3780
caaattcata tacaatgtta atgctgtatc aatattatca agattaaaaa aggtttttaa   3840
gtgttttaga acctttaata tgtccaaata taatttgttg ttacataatg catgattttt   3900
tagttgtaaa gcaatttgat tatataacca tacatttcta aatattaaac tgcataatag   3960
actttcacct ctatattcta attcttgtgt caaactacct atagattcta gactcacttt   4020
gaaatcatca agtatagtgt ttatccacgg tcccactctt aggactttct ttatactagc   4080
tgggtaatat acaccgttat gttggatcgt tttactcata aattgcatat ctcttgatat   4140
ataagtctca gttcctttta atttgtggcc tatgcctgca tactctttat acagtaattt   4200
gagactgttt aatgctagca aataatctgc ttgagcatga gtttgacctt ccatgagtct   4260
gactggttta cttatatcta ttgattgatt gtcaccatta attaaagcag taattgagaa   4320
tttccctttg agagatatta gatctaatag tgatatagct tctatggtcc atagtttttg   4380
acaccaccct tcgataccac ccatatgata tctatataat ccactttgct catctacatt   4440
gttaagatct acaatatgat cccttatata gggggtgca tgcctatatg tgcatattat   4500
tgtgacatga ggaatagtta aatgtaacca ggaaaataga gattgtacac catgcagttc   4560
atccagtaca tcactacaaa tacatgatgt ttcatatcga aatgcttgat tgaatttgct   4620
gagatctgtg atgatagagc acttactaat gtaattgttg taattatcat tgtaacgatt   4680
tgatttgtta cttattcctg ctttcaattc taatattttc tgtagttcta gatcaccata   4740
tcttgtaaga ctttcaggga aaaattgtaa aatgttttca gctatcattt tctctgctaa   4800
tatttgaact tgtctgaaca ttcctggttg cattgcaaac attctaccta cactgagttc   4860
tctttcttta cctgtcaatg ataccacatg attagggttg ttaagataac tttgattaac   4920
tacacagttg tataaatcac attcattgaa tttgttatct cttaaatagt actctaatac   4980
tcttcttgat ttatcactct cagagaattt taacttttca tgttctatat aattttgtat   5040
gtgtgacggc atataatttc tagggaaact agtccatatt aaatttttag gaggtgatat   5100
agccttatca tttatgatca tttcgagatc cacttttta ggcaatcgaa actcccgata   5160
gaaacgtagt cctgatagaa caatcaaatc tctttctgta agttccaaca aggaaggata   5220
agtgtttagt ttatagtaag ttaaccatct taagggtaaa acaatggcat tccttaaagt   5280
aggccatctg ttgtaattat ttacaaaccc ttttataatt ctatatataa aggcacctct   5340
taacatactc aaactgctta acaagtaaaa tttggtctcg ttgcaattaa ctttaacagc   5400
atccatggct tgtctttcat ctaccattgg gtgtccaaat attctgaaca aaaaatataa   5460
ttcactcaga ttgttaaggt tattgtcacc tgcaagctta attaatttta ggaacttact   5520
taatagaatt atccatctgc catttattat attatcggat actgtcttat ctaataatgt   5580
```

-continued atgacatact cttgatagca gatttttctg agctttatta gcagcatctg tgatgttgtt 5640
gagcatacta ttataaaacc gttttctgaa ttgatcttct tctgttatat ttaaaattag 5700
agacataata aatccctcta cctcttttat tatgtagaac ccctcattgt gaaatagttt 5760
tagtatacaa tctccataaa ggaataattg tgtcaagata acattattga atccacatct 5820
taagcctaag cttttattta atgtgttcaa acagttacta atccatgtaa tcaaacaaac 5880
atttaatcta ctaaggctaa tatctttcca tgtcaagaat tgattatagg ttgtcacagt 5940
aattcttttg agttccttat gataaactat acaaccatat tgattcaaaa taaattggaa 6000
tccattaaga gtatgattat ctatcaatat aaaaccatgg ttttttacct cactagatcg 6060
atactgtgtt aatatgctgt ttaattttgt gtataaatta aaccaatgta ttaaccatga 6120
tggaggatgt tgcatcgaac acattaattt cttcaagagt gttgttttga ttgtatcttt 6180
ttgttttgta gagtgatttt tgtctgcttt aagatgagat tgattatcct taacagctaa 6240
aagtatatca tctttgatta tggttgtaat aactgagttg tcttcatctt gtccattgtt 6300
ggatttaatc ttgtcttttt ctttaagccc cagtttattc agtatagcat agactttgac 6360
atcactaatt tctatagctc ttcttattat ctttttaagt aaattagtgg tagtaatctg 6420
ttctgacgag gtcatactct tgtatgtcat aagtaatgac tgaaaatagg taggttcttc 6480
tatttttatt tcacctttat gatacttaga tattaaggac tgtgttatat ttagtttctt 6540
tagatttatg tgttctatta atggattttg tctactaatt aagttggtat aatcattttt 6600
gagataagga ccattgaata tgtaacttcc taaagcatta cattctgaga aagaaataac 6660
acctttttaaa taactatcag ttagataaac attagcagaa tttccattaa taatgggatc 6720
cattttgtcc catagcttga attgtttgag ttaatagttt gatgatgtgg taagcattag 6780
gattgagtgt tatgacacta atatatatat tgtgtatata tcatcattaa tacctagatg 6840
ttgtagaaaa ttttgagttg catcaatcaa gtcttgagag gtccaatgga tttcattgaa 6900
tggttgattc ggtgagtata tatggttatt ttggttggtt tgattgatat atagtgtgtt 6960
tttttgatta tacatagtaa ctctacaact acttgttatt agtatggaat ttatactaca 7020
aggatatttg tcaggtagta tcattatttt tggcatggtc gttcgtatca ctaacagttg 7080
attcttttgg gttattgatg gttatgctct tgtggatatc caatgtgttt ttgatggttt 7140
tcttcaatac atctgccggc aatcttttta acagatgaat agtttgttta ttgtttttcc 7200
tgttgctttc aatatatgat atgacagtat tgtacactct tatcttgggt gaatttggct 7260
cttcattgtc ccttagtttt ttgatgtcat cactgttgag ttcagtgagg agtttgctca 7320
tggcaacaca tgctgattgt ttagttatat tatttattga tcctatataa ctctctagca 7380
ctccaactac accgagggca tactcttctg ttctgtccaa ctctgcagct ccacttattt 7440
ctgataaagt atctatgctt ttatccatag acttaagtat tctgtttaac ataaaatttt 7500
gtcttacaag cagtgcatgg ggtggccatt caaaataatt atgactaaaa tggcacctct 7560
tgccattcaa gcaatgacct cgaatttcaa atttgcaagg attccttcgt gacatatttg 7620
ccccagttct tatttttaca aatagtaagt taatctggta ttcaattgtt ttatataact 7680
ataaaatagg aatctactta aatagtgtaa gtgagatggt ttatagatga aagttgtgat 7740
gaagttcaaa ttttaagaaa atccaatgat agatgggtta tctatggtta gatagtgaac 7800
cattgtaaga atatgattag gtgctatttt tattcagcta ctaaatgcaa tattgtttat 7860
accactcagt tgatccttac ttagtgtgac tggtgtgctt ctggccttgc aatatagaag 7920
cagtccaact gcaattaatg ataacaatat tactataatc actataatta tagtagttat 7980

-continued

```
catgatattt gtggtggatt taccagcatt tacattatgt aataattcat ctgatttacg   8040
aataaatgct agactctggt taatcttctc attgacttga gatattgatg catcaaattc   8100
atcagagggg aacactaatg ggtcatagaa atttattatt ggttcacctt ttacatagag   8160
acttttgcct tcttgcttat ttacataata taatgtatta cctacagaca cagtatccac   8220
ccccttattt gatacataat cacacccgtt agaaaatgtc tttatgatcc cacgattttt   8280
attggatgct gtacatttag ttttgccata gcatgacaca atggctccta gagatgtgat   8340
aacggagctg cttacatctg tttttgaagt cataattttg caatcatatt tggggttgaa   8400
tatgtcaatg ttgcagagat ttacctcact tggtaatgtt aaactgttca ttgtatcaca   8460
aaatacccga tttgattgaa ctttacatgt ttcagcttgt gggaagaaag atactgatcc   8520
tgcattgtca cagtaccatc ctctgtcggt tcttgttaag cagatgttgg acccttcctt   8580
tgtgttggtt gtacatagtg gggatgtgtg cagtttccaa caaggtgtat ctattacacc   8640
atatagtggt aattgtacta catatgctaa gacttcctcc tttattatgg acatgataga   8700
gtaactttgc tgtctaacta tttgaacatt gttggacatt aactttttct gatcatttgt   8760
tataggcata tcattgatta atgataataa ttcactatta gttaacatat aagtgcttac   8820
aggtgtagtt acacctgcat tgacactaaa ttccctggta atctctagta gtctgttgtt   8880
cttttgttgg aattctatca cagtttcaat gtttgatatg ctgcagcttt gcttgttcac   8940
aataggtaac aactgtttat ctatatagtt tttgagatct aacactttgc tggttaagac   9000
actgactcca tttgataagc tgactacagc cttgtttgtg gatagtagag cacttttgat   9060
tttgttcact tccccttcta ggtgcaagac cttggatacg gcaatgccac tggcgattgc   9120
agatccaaca cctaacaaaa agccaagaaa tcttctttc ctttcttgc ttaatgttac     9180
attggtgttt ttggcattgt tgagtgtata attcataaat cttggtagtt ctcttctggc   9240
tcgattgttg gctgctggtg tgctttgcat gagcaattgt aattctgtta cagcattttt   9300
atatttatct aattcttgtt ttatcaattt taccttagcg tctgttccat tacacttatt   9360
ttccttgata gtacttaatt ctatagttat aacactagta taccaaccag ttcttagagc   9420
gctaagatag cccttgctaa ctgcactgca tgttgattga tagaattctt cagtgatgtt   9480
ttgactggaa gcgaaacaga gtgtgactgc agcaaggatt gtggtaatag catttgtttt   9540
gaggattggc aactccattg ttatttgccc catagttgat tttgattctg tttgatttgg   9600
tcatggcttt ttgcaataat acgcttttta atgactactg gtttgttgtg ttggatggag   9660
atagagattg tgataggtac tcggatgttg tatagacttg tgaagggctt ggattgcctt   9720
cggaggtggt tgagtggaga gtttcctttt gacttgtgtg ttctggattt cctgtggtgt   9780
tggaggtgag cagtgtagtt ctgatgtttg ttttggtggt gttgatggtt ggcttttctg   9840
tgggcctggt ggtaagtgct tcctttggtt ttgtggtttg aggtttgaga tctttttttgg  9900
ttgtcttgat ggttggtttt cttgtgggct tggtggtggt tttctttcca ggttttttgt   9960
ttggtattct tttgcagatg gcccagcaag ttggattgtt gctgcatatg ctgcagggta  10020
caaagttgaa cacttcaaag tgaaaatcat tatttggttt gttttgtggt ttgttttggc  10080
gttgttttgt ggtgggcttg ctgggttgta tttgggttgt tgttgtgttt ttggtcttga  10140
ctgttgtgga ttgtggggtt gacttagcac ttggtgttgt tgaagctagt gtggtggtgg  10200
gttgtgatgt agtttcggac agattggaga ggctgattcc aagctgggga ttctgggtga  10260
ggtatgttgg ggttgtgttc ttgatctggt ttgttgcatc ttgtatgatt gcagttgttg  10320
```

-continued

```
gtgtgacttt gtggtttgcc gaggctatga atatgatggc tgcaattata agtgaagttg  10380
agattatcat tgccaaaata gataatgtga tttgtgctat agatttaaga tttaacttgt  10440
ataagcacga tgatatgaat aatagatgat tgagagtgtc ccaagtcctt tctagtgtct  10500
tggcggcgcg ttggtccttg gttttggaca tgtttgcatt tgccccaatg ttgttgttgg  10560
tcttaatatt ttagttcatt gttatgacta ttttctaatt aactacttta tggtatagat  10620
gatggcttgc atggtgagac gttgatgtgg ttttgtgaag aggtgagggt agttcactta  10680
caaatgcaag gttactgttt tgagctatca gattggtgaa tgctatgtat tgactcgagc  10740
tcttggtagc tcaaaggttt tgttatggaa tatgttatat tcgcagagtt tgtttagtat  10800
tgcaatcatg atggagatta tgattagcaa agagattatt gttgttatca tgtgtattag  10860
tgtaaagtaa ggccagaatt tgcttgagaa ttctattgtt atggatgtat tttccattgg  10920
ttgattttgt ctaatgtgtt gactagtcta tgttgacaga tgttgtgatt agttggattc  10980
ctctcaatga ttatttgccc catgtggatt ttttattaac ttatttgagt actggatctg  11040
atgaacaatg acttgggatg atctgagact cctgatgagt tttgtttgat tggttgaacc  11100
acaaagggtt ggtgattacg attgtgaagt gaagaatgta ggtagaaagt ttgtatgaat  11160
caactcactg atgtagagga aaaaggttaa tcttccatgg gtttgattgc aaatcgtgta  11220
gctgtgtgct tccaatttgt tgtaacataa tatatacttt ctttttctaa gtaagctcca  11280
agatctacta tgaattgact ttgtggcttt atgtatttga atgctccttt gttgtcagtc  11340
actgtgatga ctaacagtaa tcctgagtaa gggatgattt ttgcatttgt aatagcattt  11400
ttgaattcag tggttgttat attttcaagt gtgttcagat ctttatttct gacactgatg  11460
gatctcaggt atgttggtat tatgactttt tttgatgtta ctatattttc aaattcacat  11520
aaagcaatga tgtcatgtgt tgggttgagt gttttcatag tgagatcttt aactgtagtt  11580
aacatatttt ttgattttag gcatgttaga ctgcatgcct taatttcaca gggtgtggtt  11640
acatcatatg ccagcttgct tctttcatcc aaggacacat tggcacatat ggtaaatttg  11700
ctgggcattt gcgctagcac tgcacttctt gagtttatca tgactcttaa tgatggtccc  11760
ttgggtgtgg atatttgttt cactagtata ttgacattgg ctagttcttt tataagtaaa  11820
tctgctggca tggatgattg gaacatgggc acccatattg taagtgatgc aggatcatcg  11880
tctttttcta ggacattgta ttgaacagca gctgtgtatg tggagccctc gtgaagtttg  11940
ttcacgtatg tttccatatt tgccccatct tttttgtaa ctatagtatc gattttttcc  12000
gggtggctag ttttggattg gctggttgtt tttttggctg gttggctaat cggcaaatgg  12060
atgtttggtt ggatgggtga attggtttgt ttgttagtct tctattgatg ttgtgttttg  12120
atgtgcagat aggtagctaa tcagaaatct tcaagtgata gatcattgtc actatcattc  12180
ccttccaaca ggttgttcaa tttttctgat gttggattga gagacacttc atctgatgtg  12240
tcttttgcca tcttttcact ttcctcattc ctgagtctcg ccatagcttc tagtctgtca  12300
ttggtcatta atgcttcagt tctgattttt tctatcattt cttctcttaa accaaccatg  12360
gcatctctta taccatcccg agcagatgta ggtcctgcac tcgctactac taatgtgtga  12420
agcattccta gtatttcact taatttctca tcaatcctat ctaatcttgc tgttatatta  12480
tcgtttgtct ggtcattaat ttcttcatat gaatagctag attcttcttc attgttatca  12540
aatgtttcta tggtttcttt gtatagtttt gaaaagggat tatcacttgg cgtagggtct  12600
tctttgaaac ttactagagg ttttctttga taattgggct tgttccctac agtatcatct  12660
gtctcattta ttgggtttat aatggttgaa tttgatgtta tagggctttc tttggttact  12720
```

-continued

```
tctatatcta ttgagttgac agatatgata ctatcttttt tcttgggatc tttgggtgat  12780
gtgaatttgc cctttattga ttctaggaat ttggtggctc tgttgtttgc atcttctcca  12840
tggaattcag gagcaaactt ttccatgatg ttttatttgc cccatttttt ttattaactc  12900
aaagctctac atcattatct tttggattaa gttgatgttt gatagcctct agttcttctg  12960
ctgtcaagtc taatacactg tagttaatca caccattttc tttgagttgt tcagcatatg  13020
cttttgcagc atcatataga tcttgattcc ttggtgtacc tctgtattct cccattatgc  13080
ctaggccagc agcattgcct aatactacac tagagaagtg aggaaattga gtcaaagata  13140
ataatgatgc ttttgggttg ttcaatatat ggtagaatcc tgcttctcca cccaattttt  13200
gggcatattc atacacctcc acaacctgtt ccatttctgc ttgcacacta gcgtgtccta  13260
acataatatt tttaactgat tttgctaaga ccccccaccg taacatcact tgccctgcac  13320
cataggcatt cataaacaat cctgcaaaga tcccttcaac tctactgcca cctctggtag  13380
aagattgtgc tataccaaaa tgaacaaaaa catctataaa gtgaggatat ttttcaaaca  13440
cttcatagaa gctgtttgct atatccttgg gtagtaagcc tttataacgt ttcatttcat  13500
tttttaagac attattagct ctcctaatca cagctgtaag accagatcta tcccctgctg  13560
ctaatttggt tattactaat gccgctatac ataatattat catcccacaa tcaggagagt  13620
catgcctgta ttctggagcc acctctccca tttcttttag catttttttg taggattttc  13680
tagattctat ctcaatgttg atttgaattt cagttgttaa gcttgctaat gttaacactt  13740
caaatttcat ttctttccca ttaatgtctt gacgatgtgt tgttacatcc actccatttg  13800
ctttaacatg atatcccgca tctttgagta tttttatggt gtcttctctt cctaatctag  13860
acatagcata taacatacct attaacccag tgaatttatg attagcatct tctgtgatta  13920
atagcatgcc acatagcttg ttgatgtgtt tctgcacatc ataattagga gtgtcaatgc  13980
tatctcctgt gctccgttgg atagtgtatt tgctggatga cagaagttga tctttgttga  14040
gtgtatcatt caacttgact ttgctaagag ccatttttgt atttgcccca tctttcatct  14100
tatgtctctc cttaatttta aattactata attttcaggc tccatttgga ctatggagtg  14160
tgattgtgca tgaagttatt atttcagatt gtttgaatct tgttttgaaa ttcatggatt  14220
gagatcatac ttgtatatta tgggtgtgtg cttagtaggc ttaatgccaa tgcattctaa  14280
gaacccatca tgattgataa atattggcat agggaaagtg ccatattttg tgttgtattc  14340
agtatatttt ttatatttag tgcttcccac tttgtgcaat agtttcattt catagttgac  14400
caggaatgta aatgtggcct gtctttcatc aagttttctc actatgcatt catgatttat  14460
caagtatata aatctatgtg ttatgatgtc tctggttagt gatgttatta tagtctcaag  14520
tgacaatggt ctcatgtcag tgatcatcag tctttgtggt gtggtatcat tgtgtgttgt  14580
gtccatggtt gggtcagctt agttgattta tttgccccat ttttatcttc tgtcaagttt  14640
tatattaact aatggtgtta gtgacattga tttgctagtt gatatttatt ataatttatg  14700
gattaaggtc aaatccaagt aattcagata attgattcat ataattggtc attgttgaat  14760
cacttagttt tttggagaat ttaatttcac aattgtcatc tattaggcca ttaggttgag  14820
agcaatgcgt taattccatc atttcccata tataacctcc attttgtaat actggcattg  14880
ttgtgaagtt ggatttcact acaatattat tattagggca aatatcacta cttgtaataa  14940
catgcacaaa tacaatgcca ttcaatttaa ttgtatgtat aactgcctta gccaaagcat  15000
tagttaactg tattaatttg tcagtatagc atgttatttt taacaatgct acttcatcat  15060
```

-continued tgtcaaacaa attttgcaat ctaactttta tcatactcaa tgagttgctg cccatctcta 15120
accaaaggag taaaatttaa gtggtactta tcaaattctt atttgcccca ttttttggt 15180 ttacgcaagt ttgttgtacg catttttcg cgt 15213

<210> SEQ ID NO 2
<211> LENGTH: 47
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 2
aattggtacc taatacgact cactataggg acgagaaaaa aagtgtc 47

<210> SEQ ID NO 3
<211> LENGTH: 27
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 3
ttaaacgcgt catcaaacta ttaactc 27

<210> SEQ ID NO 4
<211> LENGTH: 29
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 4
aattacgcgt taagcattag gattgagtg 29

<210> SEQ ID NO 5
<211> LENGTH: 33
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 5
ttaaggatcc gcgcgctatt attgcaaaaa gcc 33

<210> SEQ ID NO 6
<211> LENGTH: 27
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 6
aattgcgcgc tttttaatga ctactgg 27

<210> SEQ ID NO 7
<211> LENGTH: 38
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 7
ttaaggatcc gtacgttggg gcaaatgcaa acatgtcc 38

<210> SEQ ID NO 8
<211> LENGTH: 28
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 8
ttaacccggg gcaaataaaa catcatgg 28

<210> SEQ ID NO 9
<211> LENGTH: 46
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 9
aattcgtacg tattgttagt cttaatatct tagttcattg ttatga 46

<210> SEQ ID NO 10
<211> LENGTH: 32
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 10
aattcccggg atttttttta ttaactcaaa gc 32

<210> SEQ ID NO 11
<211> LENGTH: 43
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 11
ttaaacctgg taagatgaaa gatggggcaa atacaaaaat ggc 43

<210> SEQ ID NO 12

-continued

<211> LENGTH: 38
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 12
aattggatcc accaggtctc tccttaattt taaattac 38

<210> SEQ ID NO 13
<211> LENGTH: 65
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 13
aattcttaag ggaccgcgag gaggtggaga tgccatgccg acccacgcga aaaaatgcgt 60
acaac 65

<210> SEQ ID NO 14
<211> LENGTH: 28
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 14
gtccgacctg ggcatccgaa ggaggacg 28

<210> SEQ ID NO 15
<211> LENGTH: 26
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 15
acgtcctcct tcggatgccc aggtcg 26

<210> SEQ ID NO 16
<211> LENGTH: 68
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 16
tcgtccactc ggatggctaa gggaataacc ccttggggcc tctaaacggg tcttgagggg 60
ttttttgc 68

<210> SEQ ID NO 17

-continued

<211> LENGTH: 71
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 17
ggccgcaaaa aacccctcaa gacccgttta gaggccccaa ggggttattc ccttagccat 60
ccgagtggac g 71

<210> SEQ ID NO 18
<211> LENGTH: 29
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 18
ttaactcgag ttattcatta tgaaagttg 29

<210> SEQ ID NO 19
<211> LENGTH: 27
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 19
aattggtacc gggacaaaat ggatccc 27

<210> SEQ ID NO 20
<211> LENGTH: 27
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 20
ttaatctaga ttgtaactat attatag 27

<210> SEQ ID NO 21
<211> LENGTH: 31
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 21
aattggatcc ggggcaaata aatcatcatg g 31

<210> SEQ ID NO 22
<211> LENGTH: 29
<212> TYPE: DNA

<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 22
aattggatcc ggggcaaata caagatggc 29

<210> SEQ ID NO 23
<211> LENGTH: 31
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 23
ttaactcgag attaactcaa agctctacat c 31

<210> SEQ ID NO 24
<211> LENGTH: 31
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 24
aattggatcc ggggcaaata tgtcacgaag g 31

<210> SEQ ID NO 25
<211> LENGTH: 34
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 25
ttaatctaga tcaggtagta tcattatttt tggc 34

<210> SEQ ID NO 26
<211> LENGTH: 26
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 26
ttaatctaga agtaactact ggcgtg 26

<210> SEQ ID NO 27
<211> LENGTH: 44
<212> TYPE: DNA
<213> ORGANISM: Artificial
<220> FEATURE:
<223> OTHER INFORMATION: synthetic oligonucleotide -continued

<400> SEQUENCE: 27
aattggatcc ggggcaaata caaacatgtc caaaaacaag gacc 44

<210> SEQ ID NO 28
<211> LENGTH: 32
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 28
aattccatgg ggtccaaaac caaggaccaa cg 32

<210> SEQ ID NO 29
<211> LENGTH: 31
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 29
aaaagtatac ttaatgtgat ttgtgctata g 31

<210> SEQ ID NO 30
<211> LENGTH: 44
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 30
ttttgtatac tggcagctat aatctcaact tcacttataa ttgc 44

<210> SEQ ID NO 31
<211> LENGTH: 27
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 31
aatttctaga tttttaatga ctactgg 27

<210> SEQ ID NO 32
<211> LENGTH: 31
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 32
ttaatctaga cgttacgcga acgcgaagtc c 31

<210> SEQ ID NO 33
<211> LENGTH: 41
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<223> OTHER INFORMATION: oligonucleotide

<400> SEQUENCE: 33
aattaagctt accatggaca cgattaacat cgctaagaac g 41

<210> SEQ ID NO 34
<211> LENGTH: 28
<212> TYPE: DNA
<213> ORGANISM: Artificial
<220> FEATURE:
<223> OTHER INFORMATION: primer ALG018

<400> SEQUENCE: 34
ttaaaagctt tttttttttt tttttttt 28

<210> SEQ ID NO 35
<211> LENGTH: 32
<212> TYPE: DNA
<213> ORGANISM: Artificial
<220> FEATURE:
<223> OTHER INFORMATION: primer RSV126

<400> SEQUENCE: 35
aattctgcag gcccatctct aaccaaagga gt 32

<210> SEQ ID NO 36
<211> LENGTH: 44
<212> TYPE: DNA
<213> ORGANISM: Artificial
<220> FEATURE:
<223> OTHER INFORMATION: oligomer RSV011

<400> SEQUENCE: 36
agcttgcggc cgcgtcgacc cgggacgcgt cgatcgggta ccat 44

<210> SEQ ID NO 37
<211> LENGTH: 42
<212> TYPE: DNA
<213> ORGANISM: Artificial
<220> FEATURE:
<223> OTHER INFORMATION: oligomer RSV012

<400> SEQUENCE: 37
cgatggtacc cgatcgacgc gtcccgggtc gacgcggccg ca 42

<210> SEQ ID NO 38
<211> LENGTH: 31
<212> TYPE: DNA
<213> ORGANISM: Artificial
<220> FEATURE:
<223> OTHER INFORMATION: oligomer ALG32

<400> SEQUENCE: 38
agctaatacg actcactata gggagacgcg t 31

<210> SEQ ID NO 39
<211> LENGTH: 31
<212> TYPE: DNA

<213> ORGANISM: Artificial
<220> FEATURE:
<223> OTHER INFORMATION: oligomer ALG33

<400> SEQUENCE: 39
gatcacgcgt ctccctatag tgagtcgtat t 31

<210> SEQ ID NO 40
<211> LENGTH: 20
<212> TYPE: DNA
<213> ORGANISM: Artificial
<220> FEATURE:
<223> OTHER INFORMATION: primer RSV065

<400> SEQUENCE: 40
gtccattgtt ggatttaatc 20

<210> SEQ ID NO 41
<211> LENGTH: 25
<212> TYPE: DNA
<213> ORGANISM: Artificial
<220> FEATURE:
<223> OTHER INFORMATION: primer RSV093

<400> SEQUENCE: 41
caagataaga gtgtacaata ctgtc 25

<210> SEQ ID NO 42
<211> LENGTH: 19
<212> TYPE: DNA
<213> ORGANISM: Artificial
<220> FEATURE:
<223> OTHER INFORMATION: primer RSV105

<400> SEQUENCE: 42
gttggattga gagacactt 19

<210> SEQ ID NO 43
<211> LENGTH: 18
<212> TYPE: DNA
<213> ORGANISM: Artificial
<220> FEATURE:
<223> OTHER INFORMATION: primer RSV113

<400> SEQUENCE: 43
agtattaggc aatgctgc 18

<210> SEQ ID NO 44
<211> LENGTH: 20
<212> TYPE: DNA
<213> ORGANISM: Artificial
<220> FEATURE:
<223> OTHER INFORMATION: primer RSV112

<400> SEQUENCE: 44
cccagtgaat ttatgattag 20

<210> SEQ ID NO 45
<211> LENGTH: 30
<212> TYPE: DNA
<213> ORGANISM: Artificial
<220> FEATURE:
<223> OTHER INFORMATION: primer RSV160

<400> SEQUENCE: 45
aattggatcc atggacacaa cccacaatga 30

-continued

```
<210> SEQ ID NO 46
<211> LENGTH: 21
<212> TYPE: DNA
<213> ORGANISM: Artificial
<220> FEATURE:
<223> OTHER INFORMATION: primer RSV098

<400> SEQUENCE: 46

tggtagttct cttctggctc g                                              21


<210> SEQ ID NO 47
<211> LENGTH: 19
<212> TYPE: DNA
<213> ORGANISM: Artificial
<220> FEATURE:
<223> OTHER INFORMATION: primer RSV114

<400> SEQUENCE: 47

atccccaagt cattgttca                                                 19
```